United States Patent
Day et al.

(10) Patent No.: US 11,226,335 B2
(45) Date of Patent: Jan. 18, 2022

(54) METHODS FOR TARGET DNA DETECTION USING NON-FUNCTIONALIZED CARBOHYDRATE-CAPPED METALLIC NANOPARTICLES

(71) Applicant: BOARD OF TRUSTEES OF MICHIGAN STATE UNIVERSITY, East Lansing, MI (US)

(72) Inventors: Robert Day, East Lansing, MI (US); Amy Baetsen-Young, Lansing, MI (US); Evangelyn C. Alocilja, East Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 26 days.

(21) Appl. No.: 16/494,380

(22) PCT Filed: Mar. 16, 2018

(86) PCT No.: PCT/US2018/022778
§ 371 (c)(1),
(2) Date: Sep. 16, 2019

(87) PCT Pub. No.: WO2018/170348
PCT Pub. Date: Sep. 20, 2018

(65) Prior Publication Data
US 2020/0132693 A1    Apr. 30, 2020

Related U.S. Application Data

(60) Provisional application No. 62/558,421, filed on Sep. 14, 2017, provisional application No. 62/472,661, filed on Mar. 17, 2017.

(51) Int. Cl.
| | | |
|---|---|---|
| *G01N 33/58* | (2006.01) | |
| *B32B 5/16* | (2006.01) | |
| *C12Q 1/6825* | (2018.01) | |
| *C12Q 1/6834* | (2018.01) | |

(52) U.S. Cl.
CPC ............ *G01N 33/587* (2013.01); *B32B 5/16* (2013.01); *C12Q 1/6825* (2013.01); *C12Q 1/6834* (2013.01); *C12Q 2563/103* (2013.01); *C12Q 2563/155* (2013.01)

(58) Field of Classification Search
CPC ...... G01N 33/587; B32B 5/16; C12Q 1/6825; C12Q 1/6834; C12Q 2563/103; C12Q 2563/155
See application file for complete search history.

(56) References Cited

U.S. PATENT DOCUMENTS

| | | |
|---|---|---|
| 2006/0166249 A1 | 7/2006 | Rothberg et al. |
| 2012/0322064 A1 | 12/2012 | Alocilja et al. |
| 2014/0024026 A1 | 1/2014 | Alocilja et al. |
| 2014/0322823 A1 | 10/2014 | Alocilja et al. |
| 2015/0050747 A1 | 2/2015 | Alocilja et al. |

FOREIGN PATENT DOCUMENTS

WO    WO 2013/070653    *   5/2013

OTHER PUBLICATIONS

Xia et al., "Colorimetric detection of DNA, small molecules gold nanoparticles and conjugated polyelectrolytes," *Proc. Natl. Acad. Sci. USA*, 107(24):10837-41 (Jun. 2010).
Kim et al., "DNA strand exchange stimulated by spontaneo comb-type copolymer," *J. Am. Chem. Soc.*, 124(43):12676-7 (Oct. 2002).
Sharon et al., "Nanotechnology in Agricultural Diseases and Food Safety," *J. Phytology*, 2(4):83-92 (2010).
International Application No. PCT/US2018/022778, International Search Report and Written Opinion, dated Jun. 4, 2010.
Baetsen-Young et al., "Direct colorimetric detection of unamplified pathogen DNA by dextrin-cappped gold nanoparticles," *Biosensors and Bioelectronics*, 101:29-36 (2018).

* cited by examiner

*Primary Examiner* — Narayan K Bhat
(74) *Attorney, Agent, or Firm* — Marshall, Gerstein & Borun LLP

(57) ABSTRACT

The disclosure relates to a method for specific detection of a target analyte using probe DNA specific to the target analyte and non-functionalized, carbohydrate-capped metal nanoparticles such as non-functionalized, dextrin-capped gold nanoparticles. A sample mixture including a target DNA analyte and a probe DNA specific thereto is incubated to from a probe DNA-target DNA complex. The non-functionalized, carbohydrate-capped metal nanoparticles and an ionic species such as sodium chloride or other salt are added to the probe DNA-target DNA complex, and the mixture is incubated. Addition of the ionic species creates a detectable distinction, such as color of the resultant mixture, between stabilized metal nanoparticles when the probe DNA-target DNA complex is present and destabilized metal nanoparticles when the probe DNA-target DNA complex is absent. The method can be used for colorimetric detection of plant pathogens and associated diseases in agricultural production systems.

23 Claims, 7 Drawing Sheets

Specification includes a Sequence Listing.

METHODS FOR TARGET DNA DETECTION USING NON-FUNCTIONALIZED CARBOHYDRATE-CAPPED METALLIC NANOPARTICLES

CROSS REFERENCE TO RELATED APPLICATION

This application is a National Stage application of International Application No. PCT/US2018/022778, filed Mar. 16, 2018, which claims priority to U.S. Provisional Application No. 62/472,661 filed Mar. 17, 2017 and to U.S. Provisional Application No. 62/558,421 filed Sep. 14, 2017, which are incorporated herein by reference in their entireties.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "40064B_Seqlisting.txt", which was created on Sep. 16, 2019 and is 822 bytes in size. The subject matter of the Sequence Listing is incorporated herein in its entirety by reference.

STATEMENT OF GOVERNMENT INTEREST

None.

BACKGROUND OF THE DISCLOSURE

Field of the Disclosure

The disclosure relates to the use of carbohydrate-(e.g., dextrin-) capped or coated metal (e.g., gold) nanoparticles for colorimetric detection of plant pathogens and associated diseases in agricultural production systems. The physical and chemical properties of the metal nanoparticle act as a DNA-based nanosensor, enabling the colorimetric detection of a targeted gene sequence. The DNA-based nanosensor can be applied to detect targeted genes from viruses, prokaryotes, and eukaryotes, enabling the identification, for example, of both plant- and pathogen-specific traits. This approach can also be used to detect the presence of pathogen DNA from within complex samples, including those derived from plants and plant-based food products.

BACKGROUND

In many parts of the world, emerging diseases account for huge losses in human life, crops, and livestock, and thus, rapid, accurate and reliable monitoring technologies are needed to prevent further impacts on human, plant, and animal health. At present, molecular- and biochemical-based techniques, such as PCR and ELISA, are arguably the most reliable methods for the identification of plant and pathogen traits. Additionally, recent advances in genome-enabled technologies have facilitated the generation of highly specific probes to rapidly identify genetic markers for trait identification of some of the most devastating pathogens of humans and plants, including *Phytophthora infestans* (potato), *E. coli* 0157, *Magnaporthe oryzae* (rice), and *Mycobacterium tuberculosis*. However, while PCR-based assays offer sensitivity and specificity, they lack point-of-contact portability and functionality.

Over the past two decades, numerous nanoparticle-based assays have been developed which facilitate the detection of both amplified and purified genomic DNA. By exploiting the unique properties of gold nanoparticles (AuNPs), which includes highly specific spectral absorption properties, their ability to adhere to DNA, and large surface to volume ratios, AuNPs have emerged as a robust assay for colorimetric biosensing and diagnostics applications. For example, the use of surface plasmon resonance (SPR) to characterize the interaction between single stranded (ss) and double-stranded (ds) DNA by AuNPs in the presence of salt illuminates the understanding of the complex association(s) between citrate ions, DNA and AuNPs. At a mechanistic level, the DNA-AuNP interaction is mediated by the stabilization of the nucleotide-nanoparticle complex in low salt concentrations, whereas the dsDNA does not adsorb to the AuNPs and they therefore aggregate from disruption of SPR. In total, these studies have led to the development of a variety of DNA nanobioassays, each of which is designed upon salt-induced gold nanoparticle aggregation, through the use of ssDNA probe (ssDNAp) functionalized AuNPs, or unmodified citrate-capped AuNPs (c-AuNPs) with a separate DNA probe.

Several technological limitations have prevented widespread adoption of AuNP-DNA nanobiosensors, including the economical and sustainable synthesis of nanoparticles for target detection. In instances where assays and probes have been developed, the overall detection limits of these assays are still relatively low (i.e., ca. 18 ng of genomic DNA). Additionally, with an optimal reaction condition in the low molar range of salt (i.e., ca. 0.05 M), the use of AuNPs is still limited for most point-of-care assays, as many biological salt concentrations are higher than 0.1 M. In recent years, several of these limitations have been resolved, and the use of AuNPs in reaction conditions that parallel native biological conditions have been extended through the use of glyco-coated AuNPs, which has resulted in increased stability and uniformity of the modified nanoparticles, while decreasing the environmental biotoxicity. To generate greener chemistries, methods have been developed to synthesize glyco-coated AuNPs for use in diagnostic applications, such as for the detection of the chemical analyte dihydralazine sulfate in high ionic biological mediums. Similarly, a recent study demonstrated that DNA-functionalized dextrin-capped AuNPs (d-AuNPs) can be used to electrochemically detect the IS16110 gene from *Mycobacterium tuberculosis* at concentrations as low as 0.01 ng/µL using isothermally amplified DNA. Thus, the use of glyco-AuNP offers the potential for DNA detection in complex biological matrices from demonstrated enhanced stability.

SUMMARY

In an aspect, the disclosure relates to a method for detection of a target analyte, the method comprising: combining (i) a sample containing or suspected of containing a target DNA analyte (e.g., double-stranded DNA (dsDNA)) with (ii) a probe DNA that is complementary to the target DNA analyte, thereby forming a sample mixture; incubating the sample mixture under conditions sufficient to bind (e.g., hybridize) the probe DNA with (any or all) target DNA analyte present in the sample mixture, thereby forming an incubated solution comprising (i) a probe DNA-target DNA complex (e.g., dsDNApg for genomic DNA target analyte) when the target DNA analyte is present in the sample, and (ii) free (e.g., unbound or non-hybridized) probe DNA when the target DNA analyte is not present in the sample; combining the incubated solution with a non-functionalized, carbohydrate-capped (stabilized) metal nanoparticle and an ionic species (e.g., NaCl or other salt), thereby forming an (incubated) solution-nanoparticle mixture; incubating the solution-nanoparticle mixture under conditions sufficient to (i) at least partially stabilize the metal nanoparticle when the probe DNA-target DNA complex is present in the solution-nanoparticle mixture, and (ii) at least partially destabilize the metal nanoparticle when the target DNA analyte is not present in the sample; and optionally detecting a relative degree of metal nanoparticle stabilization after incubating the solution-nanoparticle mixture and/or whether the original sample contained the target DNA analyte.

In another aspect, the disclosure relates to a probe DNA-target DNA-metal nanoparticle complex comprising: a first region comprising a single-stranded probe DNA (ssDNAp) hybridized to a first strand of a double-stranded target DNA analyte (dsDNA); a second region comprising a second strand of the double-stranded target DNA analyte (dsDNA) that is not bound to the first strand of the double-stranded target DNA analyte (dsDNA); and a non-functionalized, carbohydrate-capped metal nanoparticle bound to the second strand of the double-stranded target DNA analyte in the second region.

In another aspect, the disclosure relates to a stabilized complex suspension composition comprising: water; and the probe DNA-target DNA-metal nanoparticle complex according to any of the variously disclosed embodiments herein stably suspended in the water. The suspension can generally include a stable aqueous suspension of the 3-component complex, for example including other assay components of the corresponding methods. For example, the suspension can include the buffer components for initial probe DNA-target DNA analyte binding and/or the ionic species added along with free or unbound non-functionalized, carbohydrate-capped metal nanoparticles for subsequent incubation of the assay volume.

In another aspect, the disclosure relates to a kit for detection of a target analyte, the kit comprising: a probe DNA that is complementary to a target DNA analyte; a non-functionalized, carbohydrate-capped metal nanoparticle; optionally a buffer (e.g.,); and optionally an ionic species. The carbohydrate-capped metal nanoparticle can be provided in the form of a stabilized aqueous suspension of the nanoparticles and according to any of the variously disclosed embodiments herein. The buffer can be provided as an aqueous solution or components thereof as generally defined herein. The buffer is for combination or mixing of the probe DNA and a sample to be analyzed for the target DNA analyte. The ionic species can be sodium chloride or other salt or ionic species as generally defined herein. The ionic species can be provided as an aqueous solution or components thereof. The ionic species is used for combination or mixing with the metal nanoparticle and an incubated sample mixture of the probe DNA and the sample to be analyzed.

BRIEF DESCRIPTION OF THE DRAWINGS

For a more complete understanding of the disclosure, reference should be made to the following detailed description and accompanying drawings wherein.

Figure 1:
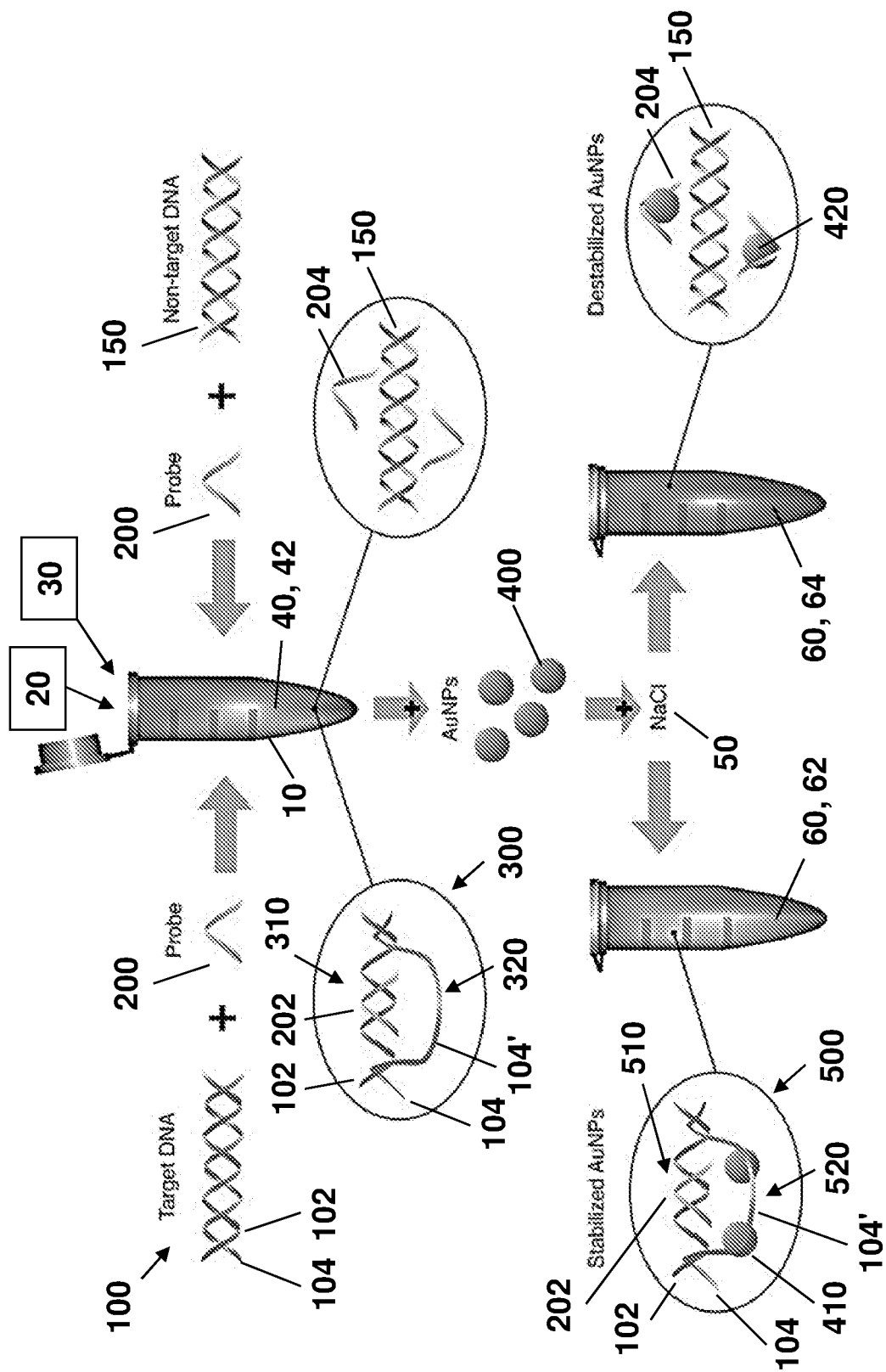
FIG. 1 is an illustration of the detection method according to the disclosure.

While the disclosed apparatus, compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

In one aspect, the disclosure relates to the use of carbohydrate-(e.g., dextrin-) capped or coated metal (e.g., gold) nanoparticles for colorimetric detection of plant diseases in agricultural production systems. The physical and chemical properties of the carbohydrate-capped metal nanoparticles (e.g., "d-AuNP" for dextrin-capped gold nanoparticles) act as a DNA-based nanosensor, enabling the colorimetric detection of a targeted gene sequence. The DNA-based nanosensor can be applied to detect targeted genes from viruses, prokaryotes, and eukaryotes, enabling the identification, for example, of both plant- and pathogen-specific traits. This approach can also be used to detect the presence of pathogen DNA from within complex samples, including those derived from plants and plant-based food products. The deployment of this rapid bioassay can enhance perception and aid precision care within resource-limited locations, thereby enabling rapid response to strengthen food security.

The carbohydrate-capped metal nanoparticles possess properties that enable them to associate with DNA. This property supports a method to colorimetrically detect small sequences of single stranded DNA, which hybridize to specific target DNA sequences. In an illustrative embodiment of the method, the DNA is extracted from an organism of interest and added to a solution with single stranded DNA probes in Phosphate Buffer Saline (PBS) with 120 mM sodium chloride. The solution is denatured at 95° C. for 5 minutes and cooled to 57.5° C. for 1 minute. Then the solution is incubated at room temperature for 10 minutes before the addition of 10 μl of a stabilized d-AuNP suspension.

In the illustrative embodiment, the dextrin-coated gold nanoparticles for the d-AuNP suspension were formed as generally described in Alocilja et al. U.S. Publication Nos. 2014/0024026 and 2014/0322823, both incorporated herein by reference in their entireties. Briefly, 20 mL of 25 g/L dextrin was mixed with 20 mL of sterile water. An addition of 5 mL of 8 g/mL $HAuCl_4$ was added to the reaction, and the pH of the solution was adjusted to 9 with sterile 10% (w/v) $Na_2CO_3$. The final volume was brought to 50 mL with water at pH 9. The reaction solution was incubated for 6 h in a darkened flask at 50° C. with continuous shaking (100 rpm). After incubation the solution turned red with a final concentration of 10 mg/mL d-AuNP.

Upon mixing the d-AuNP with the DNA reaction solution, 10 μl of 0.8 M NaCl was added and mixed in the illustrative embodiment. Next, an additional 10-minute incubation period at room temperature was conducted for color development. The reaction was interpreted as follows: A destabilization of the AuNPs turns the reaction solution blue and indicates in the presence of no target DNA. Stabilization of the AuNPs keeps the reaction solution red and indicates the presence of target DNA. The illustrative method can be used for positive detection of the oomycete plant pathogen *Pseudoperonospora cubensis* (Psc) via d-AuNP reactions with the Psc cytochrome oxidase gene. The method can detect amplified DNA from this gene, but also unamplified genomic DNA. The assay was completed as described above using the following probe sequence: 5'-TAATTGTAGTTA-CAGTATTCGTTTG-3' (SEQ ID NO: 1). Colorimetric detection of the target was recorded by camera and on a spectrophotometer (Figure X). The ratio of blue (A670—absorbance at 670 nm) to red (A520—absorbance at 520 nm) was defined to quantitatively assess the positive or negative results for (i) a water control sample, (ii) a non-target corn DNA sample, and (iii) a target *P. cubensis* DNA sample.

Recently, rapid diagnostic DNA-nanosensors have increased perception and aided precision care of human pathogens in resource-limited locations. The methods according to the disclosure illustrate a DNA-based nanosensor using dextrin-coated AuNPs or other carbohydrate-capped metal nanoparticles. Typically, AuNPs are stabilized during synthesis by a citrate coating agent, which allow absorption of DNA to the AuNP during detection. However, citrate coated AuNPs have limited shelf stability as short as one week and are easily aggregated by sodium chloride (60 mM), limiting applications to biological systems. Dextrin-coated AuNPs and carbohydrate-capped metal nanoparticles more generally overcome these limitations by increasing shelf stability to three months and resisting aggregation in moderate NaCl concentrations (0.3 M).

Terms

The term "ssDNA" includes a single free strand of polymerized deoxyribonucleic acids consisting of repeated polymer bases of adenine (A), cytosine (C), guanine (G), and/or thymine (T), where each strand has directionality and runs from five prime (5') to three prime (3')

The term "dsDNA" includes a complex of two ssDNA strands that are hybridized to each other in a complimentary fashion (adenine:thymine and cytosine:guanine), the two strands run anti-parallel to each other and form a helical structure, such that at any given end a 5'-end from one strand and a 3'-end from another strand are present.

The term "oligonucleotide" or "strand" includes a DNA molecule having from 2, 4, 6, 8, or 10 bases to 20, 50, 100, 200, 500, or 1000 bases in length and being single stranded.

The term "sequence" includes the specific nucleotide base configuration in a linear 5-prime to 3-prime order.

The term "hybridization" includes the pairing of two oligonucleotides together, where non-covalent bonding occurs between adenine and thymine or cytosine and guanine pairs, and the hybridized oligonucleotides are in opposing orientations during hybridization. Hybridization further can refer to the process of establishing a non-covalent, sequence-specific interaction between two or more complementary strands of nucleic acids into a single hybrid (e.g., via pairwise interactions between nucleic bases A=T and G≡C), which can be referred to a complex (or a duplex in the case of two strands). Hybridization can be performed by incubating a sample containing complementary oligonucleotide strands at generally mild temperatures, such about room temperature (e.g., at least 10, 15, or 20° C. and/or up to 20, 25, or 30° C., such as at about 20° C. or 25° C.). A sufficient time for hybridization is not particularly limited and generally depends on the kinetics of the binding interaction for a particular pair of complementary strands (e.g., at least 0.5, 1, 2, 5, or 10 minutes and/or up to 2, 5, 10, 20, 30, 60, 90, or 120 minutes).

The term "denaturation" (or "melting") includes a (reversible) process in which double-stranded DNA (dsDNA) unwinds and separates into single-stranded strands (complementary ssDNA). Denaturation can be performed at relatively high temperatures, for example by heating to at least 70, 80, or 90° C. and/or up to 80, 90, 95, 98, or 100° C. (e.g., at about 95° C.). A sufficient time for denaturation is not particularly limited and generally depends on the kinetics of the binding interaction for a particular pair of complementary strands (e.g., at least 0.5, 1, 2, 5, or 10 minutes and/or up to 2, 5, 10, 20, 30, 60, 90, or 120 minutes).

The term "annealing" includes the re-formation of double-stranded DNA from denatured DNA, for example between an ssDNA from an original ssDNA sample and a probe ssDNA sequence. Annealing can be performed by heating at moderate temperatures, for example by heating to at least 40, 50, or 60° C. and/or up to 50, 55, 60, 65, or 70° C. (e.g., at about 50° C., 55° C., or 60° C.). A sufficient time for annealing is not particularly limited and generally depends on the kinetics of the binding interaction for a particular pair of complementary strands (e.g., at least 0.5, 1, 2, 5, or 10 minutes and/or up to 2, 5, 10, 20, 30, 60, 90, or 120 minutes).

The term "probe" includes an oligonucleotide, generally an ssDNA probe oligonucleotide (or "ssDNAp") having a sequence selected to hybridize to the target nucleic acid or DNA (e.g., genomic DNA), which can be characteristic to a specific organism, such as a virus, bacterium, mould, fungus, plant, prokaryote, eukaryote, or other (biological) pathogen of interest.

The term "genomic DNA" (or "gDNA") includes chromosomal DNA, for example including the DNA carried in an organism for normal life-giving functions, where the set of DNA is specific and unique to each organism (e.g., virus, bacterium, mould, fungus, plant, prokaryote, eukaryote, or other (biological) pathogen of interest).

The term "AuNP" includes gold nanoparticles, which can be a solid gold sphere with a diameter of 5 to 50 nanometers.

The term "complementary" includes a second sequence of DNA bases that mirrors a first sequence, with the second sequence having the following substitutions adenine (A) in place of thymine (T), cytosine (C) in place of guanine (G), thymine (T) in place of adenine (A) and guanine (G) in place of cytosine (C) in an anti-parallel direction relative to the first sequence.

Detection Method

The disclosure relates to a method for detecting a target analyte as generally illustrated in FIG. 1. The method generally includes combining a sample 20 containing or suspected of containing a target DNA analyte 100 (e.g., double-stranded DNA (dsDNA)) with a probe DNA 200 that is complementary to the target DNA analyte 100. The target DNA analyte 100 and the probe DNA 200 can be combined, for example, in a sample or assay vessel 10 to form a corresponding sample mixture 40 including the target DNA analyte 100 and the probe DNA 200. The sample 20 can contain other non-target components, for example a non-target DNA 150 (e.g., double or single stranded) as well as other potential non-DNA components from the original sample.

The sample 20 generally can include an aliquot of any matter containing, or suspected of containing, the target analyte/nucleic acid (e.g., target or genomic DNA 100) of interest. For example, samples can include biological samples, such as samples from taken from animals (e.g., saliva, whole blood, serum, plasma, urine, tears, milk, and the like), cell cultures, plants virus, bacterium, mould, fungus (e.g., spores therefrom); environmental samples (e.g., water); industrial samples; and food samples (e.g., solid or liquid foods in raw or processed form, such as milk). Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample. Accordingly, a sample to be tested by contact with probe DNA and carbohydrate-capped metal nanoparticles can be a liquid (e.g., aqueous) medium containing or suspected of containing the analyte, where the liquid medium can be the raw sample to be tested, or it can be a liquid medium (e.g., a PBS, biological, or other buffer) to which a solid or liquid raw or prepared sample to be tested is added.

In an embodiment, the target DNA analyte 100 includes double-stranded genomic DNA (dsDNAg) characteristic of a target analyte organism. For example, the target analyte organism can be a virus, a bacterium, a mould, a fungus, or a plant. Alternatively or additionally, the target analyte organism can be a plant pathogen, for example a virus, bacterium, mould, or fungus that can damage or kill a plant, such as a plant host of the plant pathogen.

In an embodiment, the sample 20 includes a plant extract, and the target DNA analyte 100 includes a plant pathogen DNA. For example, a plant or portion thereof can be sampled and analyzed for the presence of a corresponding pathogen for the plant. This illustrated in the following examples and can include testing potentially infected cucumber plants for the cucumber plant pathogen *Pseudoperonospora cubensis*, where the target DNA analyte 100 or plant pathogen DNA is genomic DNA from *P. cubensis*. In a further embodiment, the sample 20 can include or be in the form of a crude plant extract. For example, the crude plant extract can include pulverized or ground plant material, where the resulting (liquid) extract which is analyzed as part of the sample 20 can include other non-target components, whether DNA or otherwise, and whether pathogenic or otherwise.

In an embodiment, the probe DNA 200 is a single-stranded probe DNA (ssDNAp), where the ssDNAp is complementary to a portion of one of the strands in the target DNA analyte). More specifically, the probe DNA 200 (ssDNAp) can include a first oligonucleotide sequence that is complementary to and capable of hybridizing with a region of the target nucleic acid 100 (e.g., at a first range of base positions in the target nucleic acid). The length of the first oligonucleotide is not particularly limited, but may be selected to have a suitable length such as from 5 to 100 nucleotide bases (e.g., at least 5, 10, 15, 20, or 30 and/or up to 10, 20, 30, 40, 60, 80, or 100 bases). The probe DNA 200 can be labeled (e.g., with an attached enzyme, chromogenic substrate, chromophore, radioisotope, fluorescent molecule, phosphorescent molecule, chemiluminescent molecule, metal nanoparticle, polymeric nanoparticle) or unlabeled (e.g., without any of the foregoing attached components). The probe DNA 200 suitably is unlabeled.

In an embodiment, the sample mixture 40 can further include a (pH) buffer 30, for example a buffer solution or components thereof added to an aqueous matrix of the sample matrix 20. The buffer solution 30 can generally include any suitable physiological or biological buffer, such as phosphate-buffered saline of otherwise. The sample 20, the probe DNA 200, and the buffer 30 (when present) can be combined or added to each other in any suitable manner or order. For example, the sample 20 can be added to the probe DNA 200 or vice versa. Similarly, the sample 20 and the probe DNA 200 can be added to a third component or medium, such as the buffer solution 30. In a further embodiment, the buffer 30 includes a phosphate-buffered saline (PBS) buffer or solution. The PBS buffer can include disodium hydrogen phosphate and sodium chloride at any suitable concentrations. As used and as present in the sample mixture 40 with the sample 20, probe DNA 100, and any other components added to the sample mixture 40, sodium chloride suitably is present in an amount in a range from 10 mM to 400 mM, such as at least 10, 20, 40, 60, 80, or 100 mM and/or up to 100, 150, 200, 250, 300, or 400 mM. Alternatively, or additionally, disodium hydrogen phosphate suitably is present in an amount in a range from 0.5 mM to 20 mM.

In an embodiment, the sample mixture 40 has a salt concentration of at least 40 mM. The sample mixture 40 can include one or more salts (e.g., NaCl) or other ionic species at a concentration high enough to induce aggregation of citrate-capped metal (e.g., gold) nanoparticles, such as at least about 40 mM, 60 mM, 80 mM or 100 mM NaCl or equivalent salt/ionic species. In such cases, the sample mixture suitably has a salt (e.g., NaCl) or other ionic species concentration below that which would aggregate the carbohydrate-capped metal nanoparticles 400, such as up to about 200 mM, 250 mM, 300 mM, or 400 mM NaCl or equivalent salt/ionic species. The salts or other ionic species can be part of the buffer solution 30, naturally present in the sample 20 (e.g., whether as part of a crude or raw sample or an isolated or purified sample extract), and/or separately added to the sample mixture 40. The salts or other ionic species can include a cationic species such as one or more of an alkali metal (in particular sodium or potassium), an alkali earth metal, and ammonium. Similarly, the salts or other ionic species can include an anionic species such as one or more of a halide (in particular chloride) and a polyatomic (inorganic) anions (e.g., sulfate, bisulfate, sulfite, nitrate, nitrite, carbonate, bicarbonate, among others). The foregoing concentration ranges for the salts or ionic species can similarly apply to the cationic species and/or the anionic species individually or collectively.

The sample mixture 40 is then incubated under conditions sufficient to bind (e.g., hybridize) the probe DNA 200 with any target DNA analyte 100 present in the sample mixture 40, which in turn forms a probe DNA-target DNA complex 300 (e.g., dsDNApg for a genomic DNA target analyte) when the target DNA 100 analyte is present in the sample. When the target DNA analyte 100 is not present in the sample (or present at a low, non-detectable level), free (e.g., unbound or non-hybridized) probe DNA 204 can remain, for example as well as possibly non-target DNA 150 present in the sample. The result of the incubation is illustrated as an incubated solution 42 including the probe DNA-target DNA complex 300 and/or the free probe DNA 204. In some cases, such as when the probe DNA 200 is added in relative excess to the target DNA 100 analyte, the incubated solution 42 can include both the probe DNA-target DNA complex 300 and the free probe DNA 204 in some relative amounts.

In an embodiment, incubating the sample mixture 40 to form the incubated solution 42 can include first denaturing the sample mixture 40 under conditions sufficient to denature (e.g., at least partially unwind or de-hybridize) any (e.g., at least some or substantially all) target DNA analyte 100 present in the sample mixture 40, for example to form free first strands 102 of the target DNA analyte 100 (dsDNA target analyte) and free second strands 104 of the target DNA analyte 100 (dsDNA target analyte). Denaturation can be performed at relatively high temperatures, for example by heating to at least 70, 80, or 90° C. and/or up to 80, 90, 95, 98, or 100° C. (e.g., at about 95° C.). A sufficient time for denaturation is not particularly limited, for example being at least 0.5, 1, 2, 5, or 10 minutes and/or up to 2, 5, 10, 20, 30, 60, 90, or 120 minutes. The sample mixture 40 is then annealed under conditions sufficient to hybridize any (e.g., at least some or substantially all) denatured target DNA analyte 100 present in the sample mixture 40 with the probe DNA 200, thereby forming the probe DNA-target DNA complex 300 when the target DNA analyte 100 is present in the sample. Annealing can further re-hybridize denatured/separated first and second strands 102, 104, at least at portions thereof where the probe DNA 200 is not hybridized to the target DNA analyte 100 (e.g., the first strands 102 thereof as illustrated). Annealing can be performed by heating at moderate temperatures, for example by heating to at least 40, 50, or 60° C. and/or up to 50, 55, 60, 65, or 70° C. (e.g., at about 50° C., 55° C., or 60° C.). A sufficient time for annealing is not particularly limited and can be at least 0.5, 1, 2, 5, or 10 minutes and/or up to 2, 5, 10, 20, 30, 60, 90, or 120 minutes. In this process, when target DNA analyte 100 is not present in the sample, the probe DNA 200 remains as free or unbound probe DNA 204 during the denaturing and annealing steps.

As illustrated in FIG. 1, the probe DNA-target DNA complex 300 can include a first region 310 and a second region 310. The first region 310 includes the single-stranded probe DNA 202 (ssDNAp) hybridized to the first strand 102 of the double-stranded target DNA analyte 100 (dsDNA), such that the ssDNAp 202 is complementary to a portion of the first strand 102 of the dsDNA 100 and is hybridized thereto. The a second region 320 includes a second strand 104' of the dsDNA 100 that is not bound to the first strand 102 of the dsDNA 100. More specifically, a portion of the second strand 104' of the dsDNA 100 is unbound or non-hybridized with its complementary first strand 102 in the second region 320, which also generally includes the corresponding location where the ssDNAp 202 and dsDNA 100 first strand 102 bind. Other portions of the dsDNA 100 second strand 104 can be bound to their complementary regions of the dsDNA 100 first strand 102, for example as a result of the annealing or other incubation or hybridization steps.

The incubated solution 42 is then combined with a non-functionalized, carbohydrate-capped (e.g., stabilized) metal nanoparticles 400 and an ionic species 50 (e.g., NaCl or other salt) to form a corresponding (incubated) solution-nanoparticle mixture 60. The solution-nanoparticle mixture 60 includes the probe DNA-target DNA complex 300 and/or the free probe DNA 204 as well as the added metal nanoparticles 400 and ionic species 50. The metal nanoparticles 400 and the ionic species 50 can be added to the incubated solution 42 in any suitable manner, for example together or in series (e.g., metal nanoparticles 400 first and ionic species 50 second as illustrated).

In an embodiment, the ionic species 50 combined with the incubated solution 42 and the non-functionalized, carbohydrate-capped metal nanoparticles 400 can include sodium chloride. More generally, the ionic species 50 added to the incubated solution 42 along with the metal nanoparticles 400 can be at any suitably or sufficiently high concentration that would tend to destabilize metal nanoparticles 400 that are in the presence of free or unbound probe DNA 204, such as when target DNA analyte 100 is not present (or at least at a sufficiently high level) in the sample 20 and after further incubation of the solution-nanoparticle mixture 60. Such destabilization of the metal nanoparticles 400 can induce a color or other detectable property change in the assay volume, such as a change to a (visible) blue or purple color in the case of destabilized gold nanoparticles. For example and as illustrated in the examples below, a concentration of about 250 mM NaCl is sufficient to destabilize dextrin-capped gold nanoparticles. Similarly, the added ionic species 50 does not disrupt the ability of the probe DNA-target DNA complex 300 (when present) to stabilize or maintain stabilization of the metal nanoparticles 400, allowing formation of a corresponding probe DNA-target DNA-metal nanoparticle complex 500 described below. Such stabilization of the metal nanoparticles 400 can maintain a color or other detectable property in the assay volume, such as maintenance of a (visible) pink or red color in the case of stabilized gold nanoparticles. Thus, this salt- (or ionic species-) induced differentiation includes the addition of salt or ionic species at a sufficiently high level to destabilize free metal nanoparticles 400, but at a sufficiently low level to allow metal nanoparticle 400 stabilization by the probe DNA-target DNA complex 300 in the corresponding probe DNA-target DNA-metal nanoparticle complex 500. The salts or other ionic species can include a cationic species such as one or more of an alkali metal (in particular sodium or potassium), an alkali earth metal, and ammonium. Similarly, the salts or other ionic species can include an anionic species such as one or more of a halide (in particular chloride) and a polyatomic (inorganic) anions (e.g., sulfate, bisulfate, sulfite, nitrate, nitrite, carbonate, bicarbonate, among others).

As illustrated in FIG. 1, the probe DNA-target DNA-metal nanoparticle complex 500 can include a first region 510 and a second region 510, which are analogous to the corresponding first and second regions 310, 320 of the probe DNA-target DNA complex 300. The first region 510 includes the single-stranded probe DNA 202 (ssDNAp) hybridized to the first strand 102 of the double-stranded target DNA analyte 100 (dsDNA), such that the ssDNAp 202 is complementary to a portion of the first strand 102 of the dsDNA 100 and is hybridized thereto. The a second region 520 includes a second strand 104' of the dsDNA 100 that is not bound to the first strand 102 of the dsDNA 100. More specifically, a portion of the second strand 104' of the dsDNA 100 is unbound or non-hybridized with its complementary first strand 102 in the second region 520, which also generally includes the corresponding location where the ssDNAp 202 and dsDNA 100 first strand 102 bind. Other portions of the dsDNA 100 second strand 104 can be bound to their complementary regions of the dsDNA 100 first strand 102. The complex 500 further includes stabilized metal nanoparticles 410 bound to the second strand 104' of the double-stranded target DNA analyte in the second region 520.

The solution-nanoparticle mixture 60 is then incubated under conditions sufficient to at least partially stabilize the metal nanoparticles 410 when the probe DNA-target DNA complex 300 is present in the solution-nanoparticle mixture 60, or at least partially destabilize the metal nanoparticles 420 when the target DNA analyte 100 is not present in the original sample 20. The incubation of the solution-nanoparticle mixture 60 can include essentially completely stabilization of the metal nanoparticles 410 when there is sufficient probe DNA-target DNA complex 300 relative to the added amount of metal nanoparticles 400. This is illustrated as a stabilized solution-nanoparticle mixture 62. Similarly, this can include essentially completely destabilization of the metal nanoparticles 420 when there was essentially no target DNA analyte 100 (or a very low amount thereof, such as at or near the level of detection) present in the original sample 20 and no corresponding probe DNA-target DNA complex 300 formed. This is illustrated as a destabilized solution-nanoparticle mixture 64. Incubating the solution-nanoparticle mixture 60 can be performed at mild temperatures, such about room temperature (e.g., at least 10, 15, or 20° C. and/or up to 20, 25, or 30° C., such as at about 20° C. or 25° C.). A sufficient time for incubating the solution-nanoparticle mixture 60 is not particularly limited and can be, for example, at least 0.5, 1, 2, 5, or 10 minutes and/or up to 2, 5, 10, 20, 30, 60, 90, or 120 minutes. Complete stabilization, however detected, can be used to conclude that the target DNA analyte 100 was present in the original sample 20, for example at or above a threshold concentration or amount. Similarly, complete destabilization, however detected, can be used to conclude that the target DNA analyte 100 was not present in the original sample 20, for example at or below a detection level concentration or amount. Partial stabilization and/or destabilization, however detected, can be used to determine a quantitative concentration or amount of target DNA analyte 100 that was present in the original sample 20, for example in combination with separately analyzed calibration standards.

In an embodiment, the method further includes detecting a relative degree of metal nanoparticle 400 stabilization after incubating the solution-nanoparticle mixture 600. For example, this can include detecting essentially complete stabilization, essentially complete destabilization, partial stabilization, and/or partial destabilization of the metal nanoparticles added to the assay mixture. Detecting the relative degree of metal nanoparticle stabilization can include detecting a color state of the solution-nanoparticle mixture 60 after incubation. The color state can be detected visually (e.g., with the unassisted human eye) or using suitable optical instrumentation, such as a spectrophotometer, which is particularly suitable when making a quantitative determination of the amount of target DNA analyte 100 present in the sample 20. The color state can be a maintained color state relative to the initial color of the non-functionalized, carbohydrate-capped (stabilized) metal nanoparticles 400 when initially added to the assay mixture (e.g., indicating the presence of target DNA analyte 100). Alternatively, the color state can be a changed color state relative to the initial color of the non-functionalized, carbohydrate-capped (stabilized) metal nanoparticles 400 when initially added to the assay mixture (e.g., indicating the absence of target DNA analyte 100).

Carbohydrate-Capped Metal Nanoparticles

The disclosure relates to the use of carbohydrate-capped (e.g., stabilized) metal nanoparticle compositions, in particular gold nanoparticles (AuNPs) such as solid AuNPs or nanoparticles with a gold (shell)-nanoparticle (core) structure. The metal nanoparticles can be in the form of a metal nanoparticle core stabilized by the carbohydrate capping agent (e.g., a metal nanoparticle formed substantially entirely from gold). Alternatively, the metal nanoparticles can be in the form of a nanoparticle core (e.g., non-metallic and/or magnetic) having a metal coating in a core-shell configuration (e.g., a magnetic iron oxide-gold composite particle in a core-shell configuration), where the core-shell nanoparticle is stabilized by the carbohydrate capping agent (e.g., via interactions between the metal shell and the capping agent). Compositions for use according to the disclosure include aqueous suspensions of metal nanoparticles that are stabilized with one or more carbohydrate capping agents. The nanoparticle suspensions are stable for extended periods (e.g., for at least several months) and can be used as desired at a later point in time, typically prior to use in an assay for the detection of a target biological analyte as described herein. The stable nanoparticle suspension can be formed by the aqueous reduction of metal precursor ions at non-acidic pH values in the presence of a carbohydrate-based capping agent such as dextrin or other oligosaccharides.

Metal Nanoparticle Formation: Methods of metal nanoparticle formation according to the disclosure generally are performed in an aqueous reaction system including metal ions to be reduced in solution in the aqueous medium. The metal ions in the aqueous medium are reduced at a neutral or alkaline pH value in the presence of a carbohydrate capping agent under suitable reaction conditions to form a plurality of reduced metal nanoparticles (e.g., at a reaction temperature and reaction time sufficient to convert all or substantially all of the metal ion precursors). The reaction generally includes an initial nucleation stage to form metallic nuclei followed by a longer growth stage in which metal ions reduced on the nuclei surfaces create the final metal nanoparticles. The plurality of reduced metal nanoparticles are in the form of a stabilized suspension of metal nanoparticles in the aqueous medium, where the carbohydrate capping agent stabilizes the formed nanoparticle suspension.

The specific metal ions or oxidized metal-containing species in solution and selected as precursors to the desired metal nanoparticles are not particularly limited and are suitably chosen according to a desired end use/application of the nanoparticle suspension. In an embodiment, the metal ions include gold ions (e.g., Au(III), $Au^{3+}$) and are selected to form gold metal nanoparticles (AuNPs). The metal ions can be free in solution or coordinated/coupled with other (ionic) species (e.g., $Au^{3+}$, $[AuCl_4]^-$, $[AuCl_3OH]^-$, $[AuCl_2(OH)_2]^-$, $[AuCl(OH)_3]^-$, or $[Au(OH)_4]^-$, where the oxidation level of gold in each case is +3). Other potential metal ions can include chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, and platinum. In some embodiments, two or more types of metal ions can be in solution in the aqueous medium to provide metal nanoparticles formed from alloys of two or more elemental metals. The concentration of metal ions in solution prior to reaction is not particularly limited, but it suitably ranges from 0.1 mM to 1000 mM (e.g., at least 0.1 mM, 1 mM, or 10 mM and/or up to 100 mM or 1000 mM).

The metal ions are suitably introduced into the aqueous medium as a dissolvable ionic compound, for example a salt or acid. A suitable source of gold ions is chloroauric acid ($HAuCl_4$), which can provide Au(III) in the form of $[AuCl_4]^-$. Other salts/compounds including the oxidized metal precursor such as halides (e.g., chlorides, bromides, fluorides, iodides), sulfates, sulfites, thiosulfates, nitrates, nitrites, carboxylates, sulfonates, and hydrogenated forms thereof (e.g., as in $HAuCl_4$) can be used as desired and depending on the particular metal ion to be introduced into the aqueous medium.

In some embodiments, the aqueous medium further includes, prior to reduction of the metal ions, a population of nanoparticles serving as cores/nucleation sites for deposition of the reduced metal ions, thus permitting the formation of metal nanoparticles having a core-shell structure including a nanoparticle core with a metallic shell. The nanoparticle core material is not particularly limited and can be non-metallic, metallic (e.g., different from the metal to be reduced as a shell), magnetic, etc. Magnetic nanoparticle cores are particularly useful to permit the resulting metal nanoparticle to function as both a magnetic sample/analyte separator and concentrator (e.g., due to the magnetic core) as well as a signal transducer (e.g., due to the electrical properties of the metal shell material such as gold).

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or gamma-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of gamma-$Fe_2O_3$ is Sigma-Aldrich (St. Louis, Mo.), which is available as a nano-powder having particles sized at <50 nm with a specific surface area ranging from about 50 $m^2/g$ to about 250 $m^2/g$. Preferably, the magnetic nanoparticles have a small size distribution (e.g., ranging from about 5 nm to about 25 nm) and uniform surface properties (e.g., about 50 $m^2/g$ to about 245 $m^2/g$).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, gamma-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminum oxide, chromium oxide, copper oxide, manganese oxide, lead oxide, tin oxide, titanium oxide, zinc oxide and zirconium oxide, and suitable metals include Fe, Cr, Ni or magnetic alloys.

Reduction of the metal ions in the aqueous medium is performed at a neutral or alkaline pH value, for example ranging from 7 to 12 (e.g., where the pH value is essentially constant throughout the reaction, or it may vary within the range during reaction). In various embodiments, the pH value of the reaction medium can be at least 7, 7.5, 8, 8.5, 9 and/or up to 8, 8.5, 9, 9.5, 10, 11, 12. The selection and control of the desired pH value can be effected by any suitable base and/or buffer system as is generally known in the art. As described below, in some embodiments, the pH value can be controlled by selection of a reducing agent. Non-acidic pH values, in particular those that are mildly basic or otherwise near to a physiological pH value, are desirable in certain embodiments to promote functionalization of the eventual metal nanoparticles with biomolecules that would be denatured or whose activity would otherwise be reduced or negated in an acidic environment.

The reaction temperature of the reduction process is not particularly limited, for example being at room temperature (e.g., 20° C. to 25° C.) or at mildly elevated temperatures relative to room temperature. In various embodiments, the temperature of the aqueous medium can range from 20° C. to 100° C. during the reduction reaction, for example being at least 20° C., 25° C., 30° C., 35° C., or 40° C. and/or up to 30° C., 35° C., 40° C., 50° C., 60° C., 70° C., 80° C., 90° C., or 100° C. in various embodiments.

Reduction of the metal ions in the aqueous medium is suitably effected by the addition of a chemical reducing agent to the aqueous medium. Suitable reducing agents are those that are effective at reducing metallic ions at the neutral/alkaline pH of the aqueous medium (e.g., they do not require an acidic pH and/or do not themselves create an acidic environment). In some embodiments, the reducing agent is a combined reducing agent for reducing the metal ions and pH-adjusting agent for maintaining the neutral or alkaline pH value of the aqueous medium. Suitable combined reducing and pH-adjusting agents include metal (e.g., alkali or alkali earth metal) carbonates or bicarbonates such as sodium carbonate ($Na_2CO_3$). However, other reducing agents that are operative at neutral/alkaline pH values can be used even if they do not also function as a pH-adjusting agent (e.g., in which case other non-reducing bases/buffers can be used to independently control the pH value). Examples of other suitable reducing agents include hydrides (e.g., lithium aluminum hydride ($LiAlH_4$), sodium borohydride ($NaBH_4$), diisobutylaluminum hydride (DIBAH)), dithiothreitol (DTT), sulfites/bisulfites (e.g., ammonium, metallic such as from alkali and alkali earth metals including K, Na, Li, Mg, Ba, Ca), sulfates (e.g., metallic such as from iron (II) or other soluble iron (II) salts), peroxides (e.g., those functioning as reducing agents at alkaline pH such as hydrogen peroxide ($H_2O_2$)), sulfides (e.g., metallic such as from alkali metals like Na), and amines (e.g., including ammonium salts thereof such as hydroxylamine ($NH_2OH$) or hydroxylamine hydrochloride ($NH_2OH \cdot HCl$)).

The carbohydrate useful as a capping agent according to the disclosure is generally an oligo- or polysaccharide having a plurality of saccharide residues (e.g., having a general formula $C_m(H_2O)_n$ for unmodified carbohydrates with residues derived from monosaccharides having a general formula $(CH_2O)_n$). In some embodiments, the carbohydrate capping agent can be a carbohydrate derivative, for example having additional functional groups such as carboxylate group or nitrogen-containing groups (e.g., amino, N-acetyl). The capping agent can include linear and/or branched carbohydrates, such as those including alpha- or beta-glycosidic bonds (e.g., alpha(1,4) or alpha(1,6) glycosidic linkages as in dextrin or other starch-based capping agents). The specific carbohydrate capping agent is suitably selected so that it has at least some hydrophilic character (e.g., to promote a water-stable suspension), and it can be a water-soluble carbohydrate in some refinements. In some embodiments, the capping agent is in a substantially non-oxidized form (e.g., being (substantially) free from aldose, ketose, and/or carboxylate (acid or anion) functionalities either for a portion of or the whole capping agent molecule; based on an absence of such functionalities and/or the inability to detect (non-trace) levels of the functionalities in the capping agent), for example as added to the reaction mixture, as present during reaction, and/or as bound/conjugated to the metal nanoparticles in the reaction product. In other embodiments, other non-carbohydrate capping agents such as polyethylethene glycol (e.g., or other polyether or polyethylene oxide), various silanes, polyacrylamide, and other negatively charged polymers can be used (e.g., for use instead of or in combination with other carbohydrate capping agent such as oligosaccharide; suitably in combination with a monosaccharide, a disaccharide, or a derivative thereof as described below as an additive to the carbohydrate capping agent system). The concentration of the capping agent in solution prior to reaction is not particularly limited, but it suitably ranges from 1, 2, 5, or 10 g/L to 15, 25, 35, 50, or 100 g/L (e.g., where selection of the capping agent concentration can permit selection of an average metal nanoparticle size and/or size distribution resulting from the concentration).

The capping agent is suitably an oligosaccharide having 3 to 100 saccharide residues, for example at least 3, 5, 10, 15, 20, 25, 30, or 40 and/or up to 10, 20, 30, 40, 50, 60, 80, or 100 saccharide residues. In some embodiments, the capping agent represents a plurality of oligosaccharides or polysaccharides having a distribution of sizes/lengths (e.g., in terms of number of saccharide residues). In such cases, ranges characterizing the oligosaccharide capping agent in terms of number of saccharide residues can represent an average of the distribution (e.g., number or other average), or the ranges can represent upper and lower bounds for the distribution (e.g., within 1, 2, or 3 standards deviations from the mean; representing the 1%/99%, 5%/95%, or 10%/90% cut points of the cumulative size distribution).

In some embodiments, the carbohydrate capping agent can include one or more glucose residues (e.g., D-glucose; having a plurality of glucose residues such as where the capping agent essentially consists only of glucose residues). However, the capping agent can include other saccharide residues alone, in combination with glucose, and/or in combination with each other, for example including those from allose, altrose, mannose, gulose, iodose, galactose, talose, xylose, arabinose, fucose, and/or fructose. As noted above, the capping agent can include carbohydrate derivates, for example including saccharide residues from glucuronic acid (e.g., also including salts and esters thereof), N-acetyl-D-glucosamine (e.g., derived from chitin), and D-glucosamine (e.g., derived from chitosan).

Oligomeric carbohydrate capping agents containing the various saccharide residues can be (synthetic) oligosaccharides having a selected length/saccharide sequence, or they can be formed from naturally occurring polysaccharides. Polysaccharides can be subjected to enzymatic or other chemical forms of hydrolysis to form shorter oligosaccharides, generally with an element of random size distribution. Examples of suitable precursor polysaccharides for capping agents include starch (e.g., forming dextrin), amylose, amylopectin, cellulose, laminarin, chrysolaminarin, xylan, arabinoxylan, mannan, fucoidan, and galactomannan. In an embodiment, the capping agent is a dextrin (e.g., linear, branched, or cyclic; suitably linear and/or branched having at least 10, 20, or 30 saccharide residues), for example being formed from starch (e.g., including amylose and/or amylopectin).

In an embodiment, the aqueous medium can include a saccharide-based moiety in addition to the carbohydrate capping agent during metal ion reduction. The additional saccharide-based moiety can be included to form metal nanoparticle suspensions that remain stably suspended for even longer periods (i.e., in comparison to suspensions stabilized with the capping agent alone) and can be a reducing sugar. The additional stabilizing agent is generally a monosaccharide, a disaccharide, or a derivative thereof. Suitable examples include sucrose, glucose, fructose, mannose, galactose, glyceradehyde, lactose, and maltose, although the additional stabilizing agent more generally can include any combination of the saccharide residues listed above for the oligomeric/carbohydrate capping agent.

Stabilized Metal Nanoparticle Compositions: The above process results in the formation of a metal nanoparticle composition. Once the reduction reaction has progressed (e.g., to completion, such as once substantially all precursor metal ion reactant has been consumed), the aqueous medium contains a plurality of reduced metal nanoparticles as a suspension stabilized in the aqueous medium with the carbohydrate capping agent. Accordingly, the disclosure also relates to the use of a stabilized metal nanoparticle suspension composition that includes water in a sufficient amount to provide an aqueous medium and stabilized metal nanoparticles stably suspended in the aqueous medium. The aqueous medium suspension can have the same neutral or alkaline pH as that used for metal ion reduction (e.g., ranging from 7 to 12), or it can be adjusted to a different pH value post-reduction (e.g., still generally in the neutral or alkaline range) for storage. The stabilized metal nanoparticles in the suspension individually can include a metal nanoparticle core (e.g., generally having a spherical or nearly spherical/spheroidal shape) and a carbohydrate capping agent present as a layer on an outer surface of the metal nanoparticle core in an amount sufficient to stabilize the metal nanoparticle suspension (i.e., the capping agent need not completely envelop the nanoparticle core, but it is present near the core surface in a sufficient amount to prevent/inhibit substantial settling or agglomeration of the nanoparticles). Similarly, stabilized metal nanoparticles in the suspension individually can include a core-shell nanoparticle and a carbohydrate capping agent present as a layer on an outer surface of the metal nanoparticle shell in an amount sufficient to stabilize the metal nanoparticle suspension. In various embodiments, the carbohydrate capping agent can form a complete or partial layer (e.g., a monolayer or a plurality of layers) that is adsorbed or otherwise bound to the metal nanoparticle surface such as by electrostatic interactions between the metal nanoparticle surface and hydroxyl groups of the carbohydrate capping agent present at the neutral or alkaline pH of the aqueous medium.

The population of the reduced metal nanoparticles as produced (e.g., in suspension as formed in the aqueous medium or otherwise) generally has a particle size ranging from 2 nm to 50 nm (e.g., a number-, weight-, or volume-average particle size). For example, the average size of the nanoparticle distribution can be at least 2, 5, 8, 10, 12, or nm and/or up to 8, 10, 12, 15, 20, 25, 30, 40, or 50 nm. In an embodiment, the distribution of metal nanoparticles also has a relatively narrow size distribution, for example a substantially normal size distribution with a standard deviation of 25% or less relative to the average particle size of the distribution (e.g., a monomodal distribution; having a $\sigma/\langle x \rangle$ for a normal distribution of not more than 25%, 20%, 15%, or 10% and/or at least 1%, 2%, 5%, 8% or 10%). Various size parameters of the metal nanoparticle distribution (e.g., average size, distribution width) can be selected/controlled by selecting one or more reduction reaction parameters. Examples of suitable reaction/operating conditions that can be selected to control nanoparticle size include capping agent concentration, metal ion concentration, reducing agent concentration, reaction temperature, reaction pH, length and/or size distribution of the oligomeric capping agent.

The capping agent-stabilized metal nanoparticles remain stably suspended in the aqueous medium for extended periods without (substantial) settling or agglomeration of the nanoparticles. For example, the suspension can remain stable for at least 90 days when stored at room temperature. In various embodiments, the suspension is stable or capable of remaining stable for periods of at least 90, 120, 180, 270, or 360 days and/or up to 270, 360, 720, or 1080 days and/or at storage temperatures generally between 20° C. and 25° C., in particular at a neutral or alkaline pH. The metal nanoparticles remain stably suspended in the aqueous medium in part based on the hydrophilic character of various functional groups the carbohydrate capping agent (e.g., hydroxyl groups, which can impart a water-soluble character to low-molecular weight capping agents).

The capping agent-stabilized metal nanoparticles are suitably non-functionalized. The nanoparticles are suitably free from biomolecules or specific binding pair members which specifically bind to a target analyte (e.g., a protein, virus, bacteria, ssDNA, such a DNA of a target microorganism or complementary ssDNA). A specific binding pair member generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, biomimetic antibody-antigen (e.g., molecularly imprinted synthetic polymer having specific binding capability with the antigen), and whole cells are not immunological pairs, but can be considered as binding pair members within the context of the present disclosure. Such biomolecules or specific binding pair members are often attached to nanoparticles by one or more of physical adsorption (e.g., resulting from electrostatic metal-biomolecule interactions), direct binding (e.g., based on affinity interactions between the metal and a functional group of the biomolecule, such as between a thiolated biomolecule and gold), covalent attachment (e.g., between the biomolecule and a covalent linking intermediate that is bound to the metal nanoparticle, such as through thiolated carboxylic acids, EDAC-mediated attachment of biomolecules, biotin-streptavidin linking, and azide-linking or other "click" functionalization techniques). Thus, in an embodiment, the capping agent-stabilized metal nanoparticles can be free from such attachments to other moieties besides the carbohydrate capping agent(s), whether a biomolecule, a specific binding pair member, or otherwise, for example as bound to an outer surface of the metal nanoparticle and/or to the carbohydrate capping agent.

EXAMPLES

The examples illustrate the disclosed methods and compositions, but are not intended to limit the scope of any claims thereto. In particular, the examples illustrate methods of using non-functionalized carbohydrate-capped metal nanoparticles to detect a target analyte, in particular a target DNA analyte.

This example illustrates an unamplified genomic DNA (gDNA) nanosensor using dextrin-capped AuNPs (d-AuNPs), exploiting dispersion and aggregation characteristics of d-AuNPs, in the presence of gDNA, for sequence-specific detection. The d-AuNPs are stable in a five-fold greater salt concentration than citrate-capped AuNPs and the d-AuNPs were stabilized by single stranded DNA probe (ssDNAp). However, in the elevated salt concentrations of the DNA detection assay, the target reactions were surprisingly further stabilized by the formation of a ssDNAp-target gDNA complex. Without being bound by a particular theory, it its believed that genomic ssDNA secondary structure formation during ssDNAp-to-target gDNA binding enables d-AuNP stabilization in elevated ionic environments. This example illustrates detection of as little as 2.94 fM of pathogen DNA, and using crude extractions of a pathogen matrix, as few as 18 spores/µL. The highly specific and rapid assay described herein represents an inexpensive visual DNA detection device for resource-limited locations.

This example used d-AuNPs to detect a specific unamplified DNA sequence of *Pseudoperonospora cubensis*, the causal agent of economically important cucurbit downy mildew. Previous reports have demonstrated the use of functionalized d-AuNPs to electrochemically signal DNA target capture; however, this example illustrates colorimetric, sequence-specific, unamplified gDNA detection using unmodified or non-functionalized d-AuNPs. Salt-induced aggregation of citrate- and dextrin-capped AuNPs was compared with and without a ssDNAp. The DNA-d-AuNPs interactions permits a sequence-specific gDNA-based detection assay utilizing the interactions of ssDNA, dsDNA and d-AuNPs in an elevated ionic environment. Using a combination of UV-Vis absorption spectra, aggregation ratios, and transmission electron microscopy (TEM), interactions between the method components can be characterized.

Biological reagents: Genomic DNA and sporangia from the plant pathogenic oomycete *Pseudoperonospora cubensis* (target analyte/DNA) and its cucumber host, *Cucumis sativus* cv Eureka (non-target analyte/DNA), were used. The ssDNA oligonucleotide 5'-AATCACAGCTTCTATGTTT-TACAT-3' (SEQ ID NO: 2) used as the probe DNA complementary to the target DNA was synthesized by Integrated DNA Technologies (Coralville, Iowa).

Gold nanoparticle synthesis: Dextrin-capped gold nanoparticles (13 nm in diameter) were prepared according to the method of Alocilja et al. U.S. Publication Nos. 2014/0024026 and 2014/0322823. In brief, 5 mL of 20 mM $HAuCl_4$ was added to 20 mL of 25 g/L of dextrin stock in a 250-mL flask. The pH of the solution was adjusted to 9.0 with 10% sodium carbonate ($Na_2CO_3$) and the final reaction volume was adjusted to 50 mL with sterile distilled water (pH 9.0). Particle formation occurred as the flask was incubated at 50° C. for 8 hours in the dark. The synthesized nanoparticles were evaluated by TEM using a concentration of d-AuNPs of $7.6 \times 10^{-9}$ M. This value was derived from Beer's Law based on a molar extinction coefficient of $2.7 \times 108$ $M^{-1}cm^{-1}$ for 13 nm AuNPs. Citrate-capped gold nanoparticles (c-AuNPs) (10 nm, $9.93 \times 10^{-9}$ M) were obtained from Cytodiagnostics (Ontario, Canada).

DNA extraction: Genomic DNA was extracted from 100 μL of *Pseudoperonospora cubensis* sporangia isolated from infected cucumber plants using the Machanery Nagel Nucleospin DNA Kit (Duren, Germany). In brief, sporangia were flash frozen in liquid nitrogen and homogenized in a tissue grinder for 40 seconds at 4.0 M/S using a FASTPREP-24 tissue homogenizer (MP-Biomedical, Santa Ana, Calif.). DNA was further purified according to the manufacturer's protocol and quantified by QUBIT (fluorometric detection; ThermoFisher, Waltham, Mass.). The extracted DNA was stored at −20° C. until use. For non-target DNA reactions, gDNA was extracted from five cucumber leaf discs collected using a #3 cork borer (1 $cm^2$) and flash frozen in liquid nitrogen. DNA was isolated and purified as described above.

Procedure: To evaluate the stability of the dextrin- and citrate-capped AuNPs in the presence and absence of a 66 nM ssDNAp, 20 μL of NaCl (0, 50, 100, 150, 200, 250, and 300 mM final reaction concentration) was added to 10 μL of each of the AuNPs. After a 10-minute incubation at 21° C., the visible absorption spectrum of the d-AuNP aggregation was quantified as described below. ssDNAp-to-target hybridization was initiated by the addition of 2 μL of 1 μM ssDNAp and 5 μL of a 23 fM solution of *P. cubensis* (target analyte/DNA) or 4 fM *C. sativus* (non-target analyte/DNA) extracted gDNA in hybridization buffer [10 mM phosphate buffered saline (PBS) at 0.4 M NaCl (pH 7.0)]. Next, the reaction was denatured at 95° C. for 5 min, followed by annealing for 1 minute at 57.5° C. The reaction was cooled for 10 minutes at 21±1° C. before adding 10 μL of d-AuNPs, followed by 10 μL of 0.8 M NaCl to initiate particle aggregation (NaCl is further denoted as salt). The reaction was then incubated for 10 minutes at 21° C., and the aggregation of AuNPs was quantified by measuring the absorption spectrum of the reaction from 400 to 700 nm.

Characterization of AuNP aggregation: PCR tubes (200 μL) were used as a reaction vessel. A SPECTRAMAX M2E plate reader (Molecular Devices, Sunnyvale, Calif.) was used to measure the 520 nm and 620 nm absorbance values for AuNPs salt and oligonucleotide interactions and genomic DNA sensitivity in a 96 well 200 μL plate. A NANODROP 2000 spectrophotometer (Thermo-Fisher, Waltham, Mass.) was used to assess the UV-vis absorption spectrum for ssDNA oligomer-to-target hybridization and crude matrix sensitivity. Means of aggregation were separated with a one-way ANOVA using aov in CRAN.R-project. Means were separated at P≤0.05 using Tukey's honestly significance difference test. Particle dispersion was determined by TEM images and were collected with a JEOL 100CS TEM from 20 μL final reaction volumes containing d-AuNPs in water, in 66 nM ssDNAp, in 66 nM ssDNAp in the presence of 4 fM non-target gDNA, and in 66 nM ssDNAp in the presence of 29 fM target gDNA. All reactions were conducted in 1.5 mM PBS containing 60 mM NaCl. Reactions were incubated at 95° C. for 5 minutes, followed by annealing for one min at 57.5° C., and then cooled for 10 min at 21° C. d-AuNPs (10 μL) were added to cooled reactions.

Detection of unpurified pathogen extracts: *Pseudoperonospora cubensis* sporangia were serial diluted in sterile microcentrifuge tubes in amounts ranging from 185 to 1.85/μL in 200 μL of hybridization buffer. Samples were pulverized using 3 mm glass beads, and 5 μL of the resultant sporangial extract from each serial dilution was used in the in the AuNP assay. All samples were analyzed in triplicate.

Results for AuNP-DNA interactions: The example illustrates a DNA-nanobiosensor colorimetric detection assay that exploits the interaction(s) between DNA and d-AuNPs or other carbohydrate-capped metal nanoparticles. As shown in FIG. 1, assay specificity relies on the induced stability of d-AuNPs in the presence of sequence-specific gDNA targets. Using this approach, a denatured gDNA target was hybridized with a complementary sequence-specific ssDNAp, thereby exploiting the electrostatic and hydrophobic properties of generated genomic ssDNA (ssDNAg) and dsDNA of the probe-target complex (dsDNApg). This approach revealed that d-AuNPs stabilized the ssDNAg complex under high ionic conditions. It was thought that under high ionic conditions, a ssDNAp would bind to denatured target gDNA, displacing a ssDNAg, which in turn, through electrostatic interactions, would generate a ssDNAg stabilized d-AuNP complex. Thus, in the presence of non-target gDNA in a higher salt environment, the ssDNAg adsorption to AuNPs will lead to moderate aggregation and differentiation from greater destabilization of d-AuNPs bound with ssDNAp.

Figure 2:
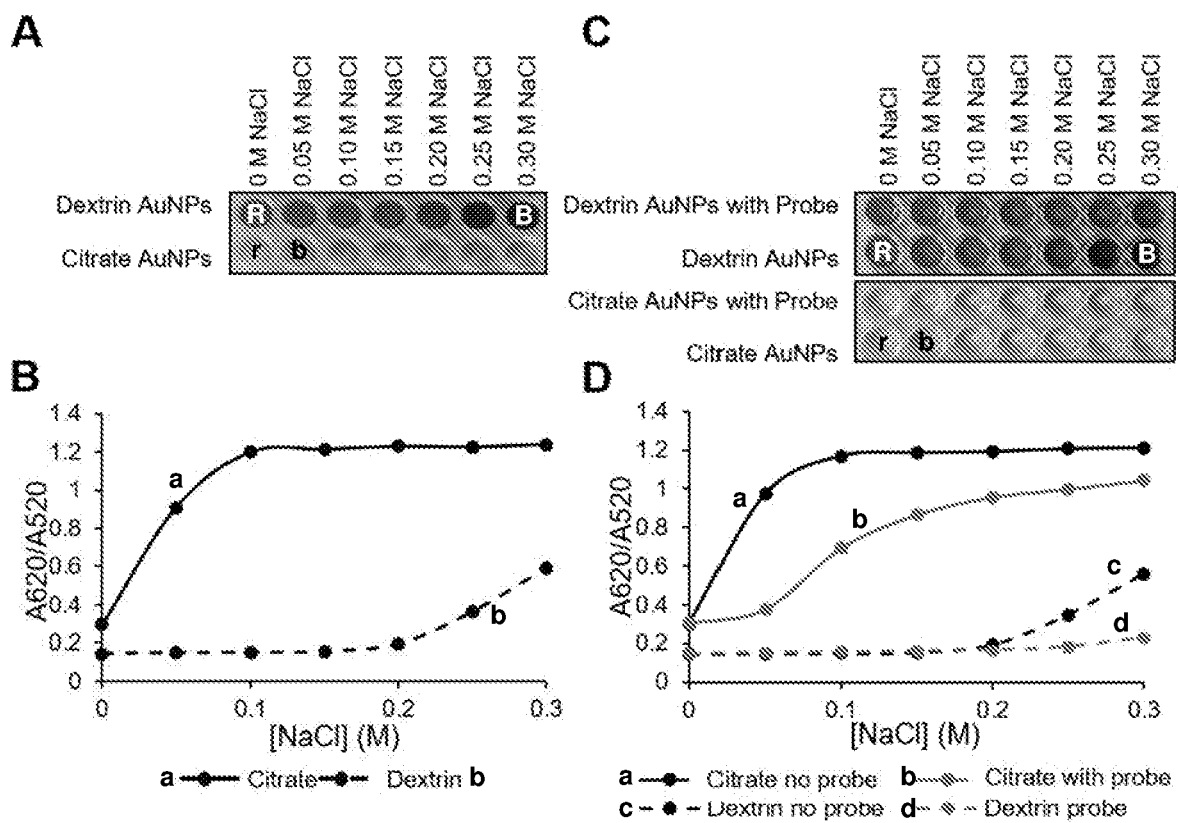
FIG. 2 includes photographs and graphs illustrating that dextrin-capped AuNPs (d-AuNPs) resist aggregation at elevated NaCl concentrations and are stabilized in the presence of ssDNA. A. Photograph of citrate and d-AuNPs solutions with increasing salt concentration. B. Aggregation of citrate- and d-AuNPs in the presence of increasing NaCl concentrations. C. Visualization of citrate- and d-AuNPs solutions with increasing NaCl concentration, with and without a ssDNA probe. D. Aggregation of citrate- and d-AuNPs with and without ssDNA probe with increasing salt concentration. In panels A and C, a superimposed "R" indicates a red color, a superimposed "B" indicates a dark blue or purple color, a superimposed "r" indicates a light red or pink color, and a superimposed "b" indicates a light blue color.

Reduced aggregation: Previous studies have demonstrated the function and utility of citrate-capped AuNPs in a variety of diagnostic applications. This example illustrates the impact of salt concentration on the aggregation of d-AuNPs, and from this, optimized a method using salt-induced AuNP aggregation for a dsDNApg-containing reaction. To do this, and as shown in FIG. 2, the stability of citrate- and dextrin-capped AuNPs was analyzed over a salt gradient ranging from 0 to 300 mM to identify concentrations critical for AuNP aggregation. A visible color change (i.e., from red to blue) was observed at NaCl concentrations ranging between 50 mM and 250 mM for both the citrate- and dextrin-capped AuNPs, respectively (FIG. 2, panel A). This difference was highlighted by a concomitant increase in AuNP aggregation (the ratio of absorbance at 620 and 520 nm; A620/A520), indicated by a shift from the gold SPR peak at 520 nm to 620 nm with increasing concentrations in NaCl (FIG. 2, panel B).

AuNP salt-induced aggregation results from inter-particle plasmon coupling during the reduction of electrostatic forces between particles. This example demonstrates that the SPR of c-AuNPs was disrupted by the addition of 40 to 60 mM of salt, a result previously observed. As shown, however, d-AuNP aggregation was not observed until a much higher final concentration of 250 mM NaCl was achieved, indicating that the dextrin capping agent stabilized AuNP SPR. Similar previous results were observed using dextran-capped AuNPs at NaCl concentrations as high as 100 mM NaCl. In total, these data demonstrate that glyco-coating of AuNPs facilitate a reduction in NaCl-induced aggregation of AuNPs.

To determine if dextrin-capping agent altered ssDNAp adsorption to AuNPs, thereby affecting salt-induced aggregation, the interaction(s) between oligonucleotide-d-AuNPs and DNA were investigated. As a point of comparison, c-AuNPs were used in parallel reactions, as these AuNPs have previously been shown to adsorb ssDNAp, a function that stabilizes the colloidal state of the reaction. As shown in FIG. 2 (panel C), a reduction of salt-induced aggregation of d-AuNPs was observed, as indicated by the maintenance of a red hue in the reaction, when comparing citrate-capped and d-AuNPs over a 300 mM salt concentration range. Similarly, the addition of ssDNAp resulted in further decreased aggregation of both citrate-capped and d-AuNPs in higher salt concentrations; this result was not observed when the AuNPs were incubated in the absence of the ssDNAp. As shown in FIG. 2 (panel D), a shift in absorbance to 620 nm was delayed in the ssDNA oligomer treatments in both AuNPs resulting in a lower aggregation ratio. This observation suggests that ssDNAp adsorbs, and further stabilizes, the AuNP colloidal state independently of the surface chemistry. Similarly, unmodified d-AuNPs were previously found to become as efficiently functionalized with thiol modified ssDNAp as c-AuNPs, illustrating that the surface chemistry of the AuNPs did not alter functionality. Moreover, the observed reduced aggregation of d-AuNPs at higher salt concentrations provides supporting evidence that d-AuNPs adsorb to the ssDNAp in a similar manner as c-AuNPs. Based on these data, it is thought that d-AuNPs and other carbohydrate-capped metal nanoparticles can be utilized in an unmodified state to detect target DNA sequences much in the same manner as c-AuNPs, yet in higher ionic environments than possible with c-AuNPs.

Figure 3:
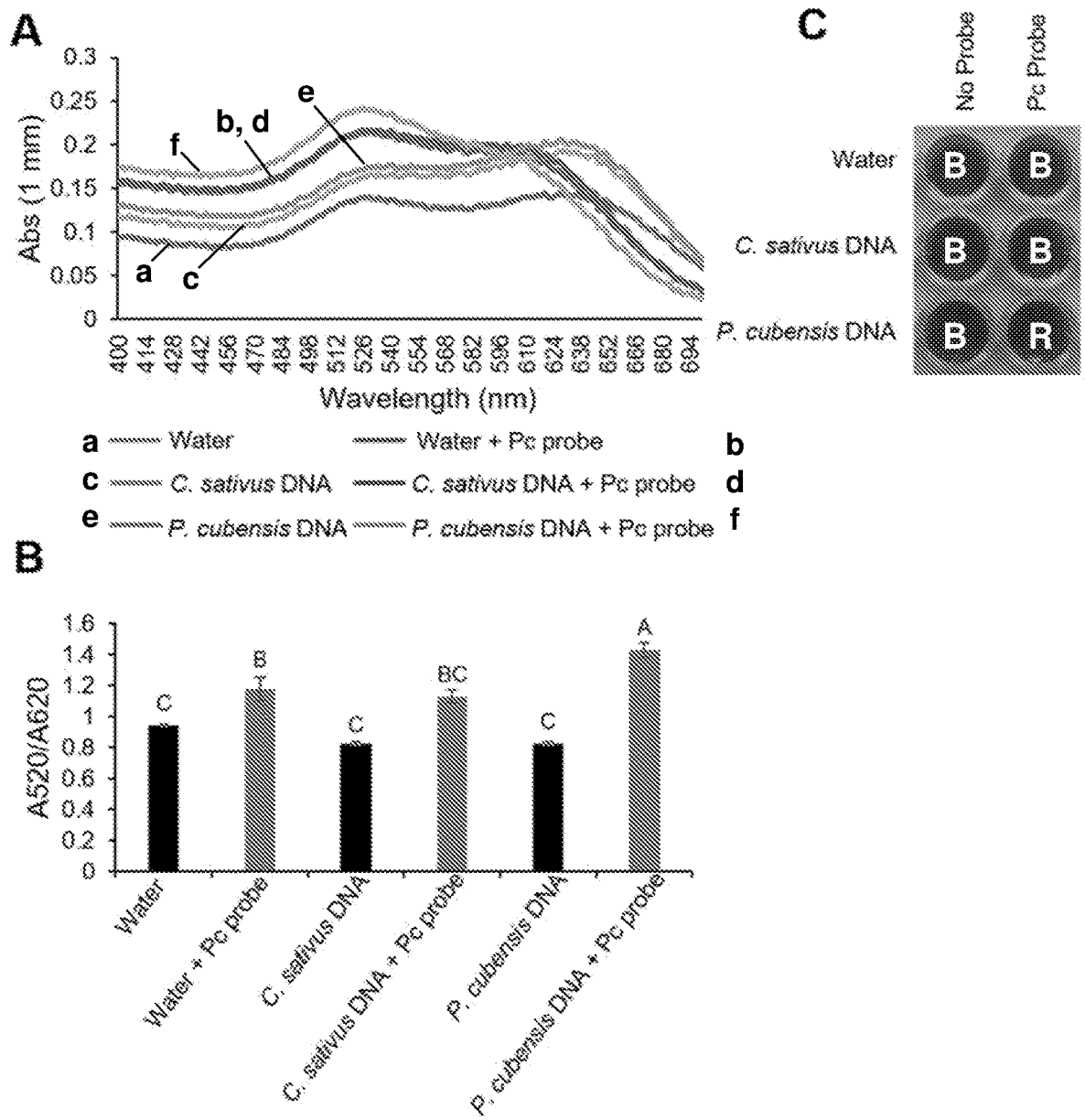
FIG. 3 includes photographs and graphs illustrating that complementary genomic DNA (gDNA) target stabilizes dextrin-capped AuNPs (d-AuNPs) in the presence of NaCl. A. UV-vis absorption spectrum of d-AuNPs in the presence of water, ssDNA *P. cubensis* (Pc) probe (ssDNAp). B. Corresponding aggregation d-AuNPs. C. Visualization of DNA-d-AuNP reactions. In panel C, a superimposed "B" indicates a blue color, and a superimposed "R" indicates a reddish-blue or maroon color. Bars represent means ±standard error of the mean. Means within each treatment followed by different letters are significantly different at $P \leq 0.05$ according to Tukey's honestly significant difference test.

Specificity: As noted above, the optical properties of unmodified AuNPs in the presence of DNA enables sequence-specific DNA detection by differentiation with salt. The example illustrates the DNA-AuNP interaction and the corresponding colorimetric differentiation between ssDNA and dsDNA under ionic conditions. Based upon this, a DNA sequence-specific assay was developed to examine ssDNA and dsDNA interactions with d-AuNPs. The development of a hand-held assay resulted in an increase of aggregation of the d-AuNPs (FIG. 3) due to increased quantification time when compared to salt optimization (FIG. 2). As shown in FIG. 3 (panel A), gDNA presence, as well as reactions containing no DNA, resulted in a visual colorimetric shift of d-AuNPs towards 620 nm, indicating a disruption of d-AuNP SPR by the salt. Additionally, a disruption of d-AuNPs aggregation by gDNA was not observed in the presence of salt (FIG. 3, panel B), an observation similar to previous results using citrate-capped AuNP and dsDNA. As noted above, ssDNAp alone, or when mixed with non-target gDNA, showed a distinguishable absorbance profile at 620 nm while maintaining a similar reduced SPR peak at 520 nm (FIG. 3, panel A), a process that stems from ssDNAp adsorbing to the d-AuNPs, preventing total aggregation (FIG. 3, panel B). Conversely, a statistically enhanced SPR peak was observed at 520 nm ($P \leq 0.05$) when the target gDNA and ssDNAp interacted, compared to the aforementioned reaction, or in reactions containing non-target gDNA-ssDNAp combinations. Taken together, these data demonstrate the high specificity of the reaction, and moreover, support a mechanism whereby a reduction of d-AuNP aggregation in samples containing both ssDNAp and target gDNA leads to enhanced stabilization of d-AuNPs, a reaction that is visually distinguishable without any instrumentation (FIG. 3, panel C).

The observation of an increase in the overall stabilization of d-AuNPs by the ssDNAp and complementary gDNA target was surprising, as previous studies using c-AuNPs reported that aggregation is not disrupted when ssDNAp binds to the DNA target. The simplest explanation for this apparent discrepancy stems from divergence of the citrate-capped gold nanoparticle salt-induced aggregation by the dextrin surface chemistry and increased salt concentration. However, the results shown in FIG. 2 demonstrate that ssDNAp adsorbs to d-AuNPs, and previous results demonstrated that dextrin capping did not alter AuNP binding of ssDNAp, including thiol modified ssDNAp. Thus, it is thought that the direct interaction of the dextrin surface chemistry with DNA is not responsible for stabilization of the d-AuNPs in the presence of the ssDNAp and the target gDNA.

The results support the hypothesis that the dextrin-capping agent enhances the stability of AuNPs under high ionic conditions, even more so than c-AuNPs (FIG. 2). In fact, the d-AuNP assay illustrated in this example can be performed in a five-fold greater ionic concentration than is typically conducted for c-AuNPs-DNA detection assays. With increasing salt concentrations, DNA-DNA and DNA-AuNP interactions change by quenching destabilizing negative charges on the phosphodiester DNA backbone and promoting DNA base stacking. This indicates that non-native secondary structures likely form when the ssDNAp and complementary target bind, creating a secondary structure with the non-binding strand of gDNA. The addition of d-AuNPs into an elevated ionic solution could increase the rate of ssDNA adsorption, thereby creating a more favorable environment for d-AuNPs to bind to gDNA secondary structures. In total, this reaction could lead to enhanced stabilization of the d-AuNPs upon ssDNAg secondary structure target-complex formation, more than ssDNAp alone (FIG. 3).

Figure 4:
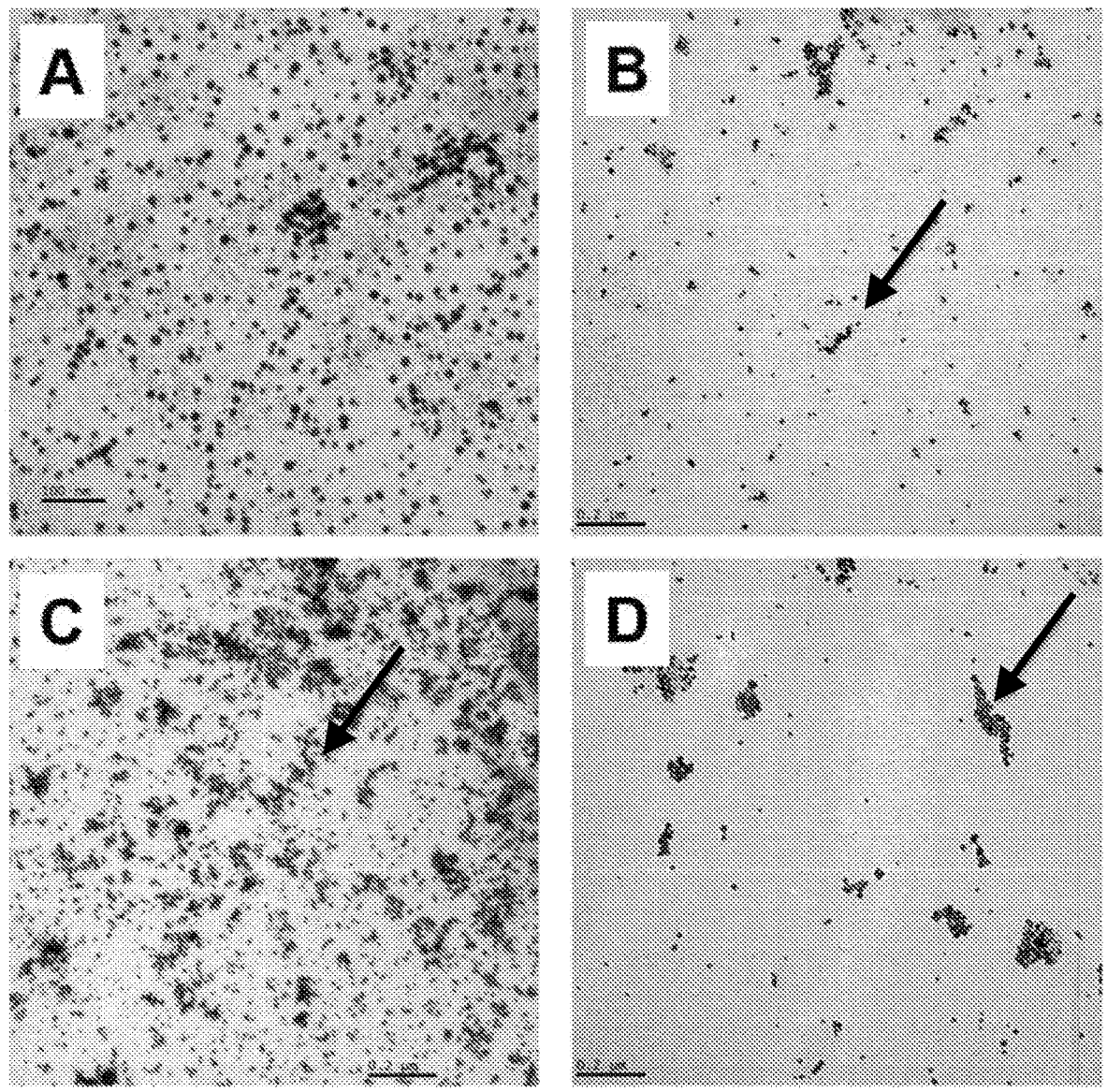
FIG. 4 includes transmission electron microscopy images of dextrin-capped AuNPs (d-AuNPs) dispersion in the presence of genomic DNA (gDNA). A. d-AuNPs+water only control. Bar=100 nm; B. d-AuNPs+ssDNA probe (ssDNAp). Bar=200 nm; C. AuNPs+non-target gDNA and ssDNAp. Bar=200 nm; D. d-AuNPs+target gDNA-ssDNAp complex. Bar=200 nm.

Stabilization: AuNP-DNA interactions can be visualized through aggregation-dispersion characteristics of individual AuNPs. AuNP size, aggregation clustering, or shape will change upon bias of DNA interaction. Therefore, to test if the physical interaction of the ssDNAp and gDNA target stabilized the d-AuNPs, the dispersion of d-AuNPs was investigated following ssDNAp annealing to denatured gDNA before salt induced aggregation by using TEM. As shown in FIG. 4 (panel A), a uniform dispersion of d-AuNPs was observed in the absence of DNA interactions. However, in the presence of a ssDNAp, a slight aggregation of AuNPs was observed (FIG. 4, panel B). A similar dispersion pattern to the ssDNAp treatment was observed in the non-target gDNA-ssDNAp treatment (FIG. 4, panel C) with dispersed gatherings of single d-AuNPs and larger random aggregates. However, when AuNPs were incubated in the presence of the target gDNA-ssDNAp, enhanced aggregation of AuNPs was observed, with few single, un-aggregated, d-AuNPs (FIG. 4, panel D). These data suggest that d-AuNPs aggregate in the vicinity of target gDNA strands displaced by the ssDNAp. The example supports the hypothesis that d-AuNP physical aggregation is enhanced (i.e., d-AuNPs stabilized) within these ssDNAg environments.

Figure 5:
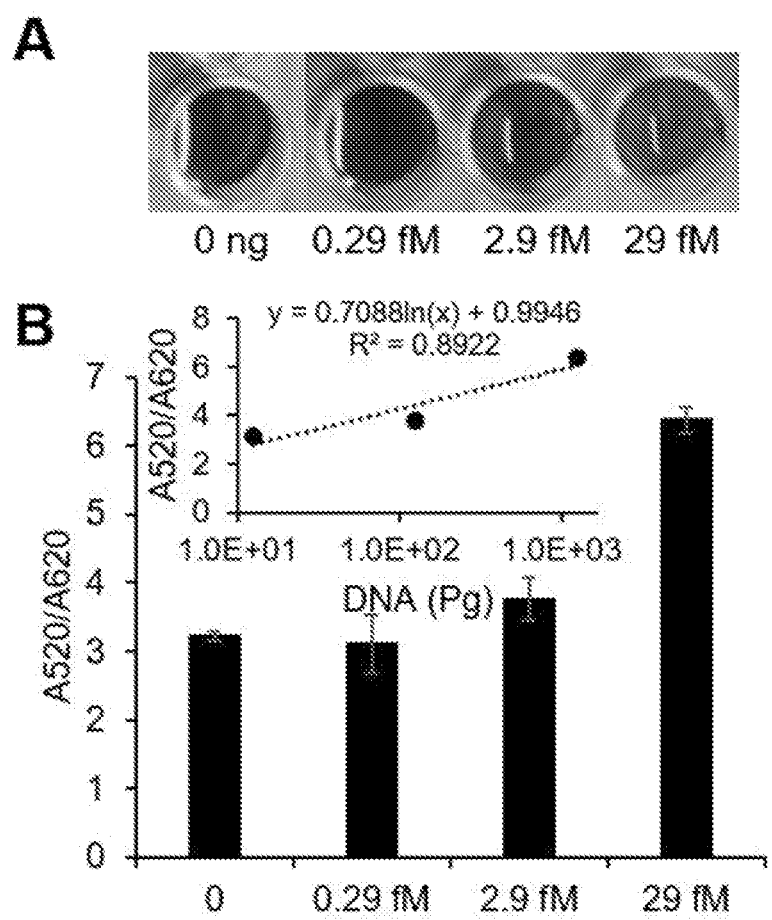
FIG. 5 includes photographs and graphs illustrating the sensitivity of the colorimetric dextrin-capped AuNPs (d-AuNPs) nanobiosensor assay with *Pseudoperonospora cubensis* extracted genomic DNA. A. Photograph d-AuNP visual aggregation. B. Aggregation response of serially diluted DNA. Bars represent means ±standard error of the mean of three reactions. The inset depicts the linear range of the DNA detection assay.
Figure 6:
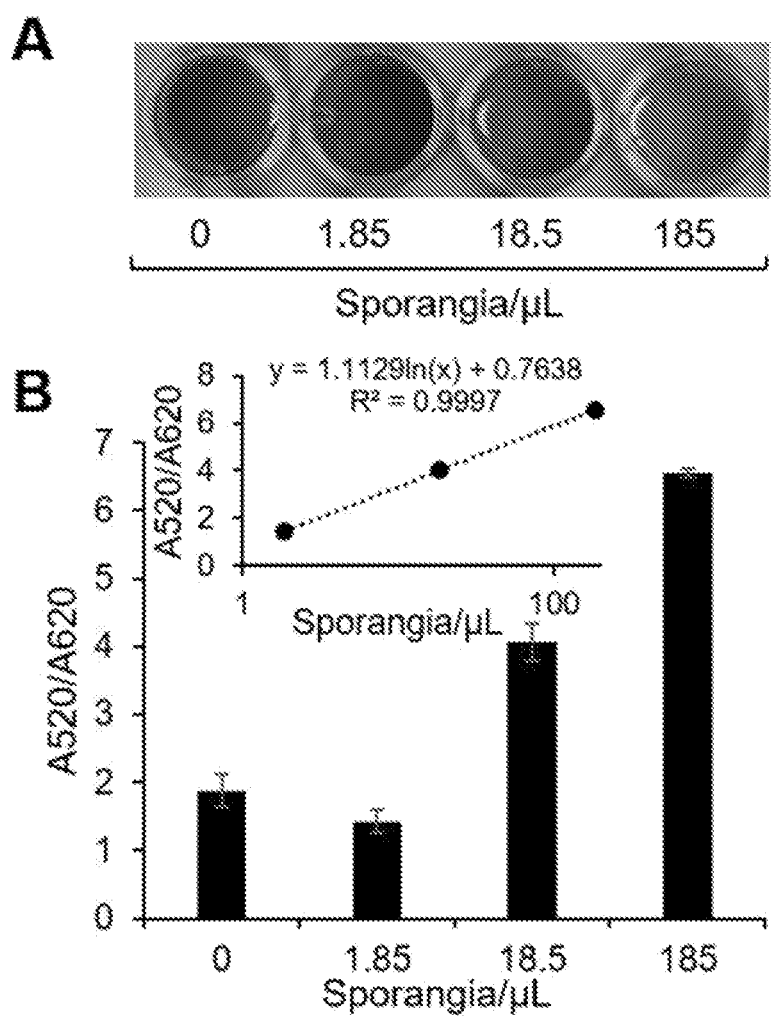
FIG. 6 includes photographs and graphs illustrating the colorimetric crude detection of *Pseudoperonospora cubensis* DNA. A. Photograph dextrin-capped AuNP visual aggregation. B. Aggregation of dextrin-capped AuNPs serially diluted sporangia from *P. cubensis*. Inset graph demonstrates the linear range of the detection assay.
Figure 7:
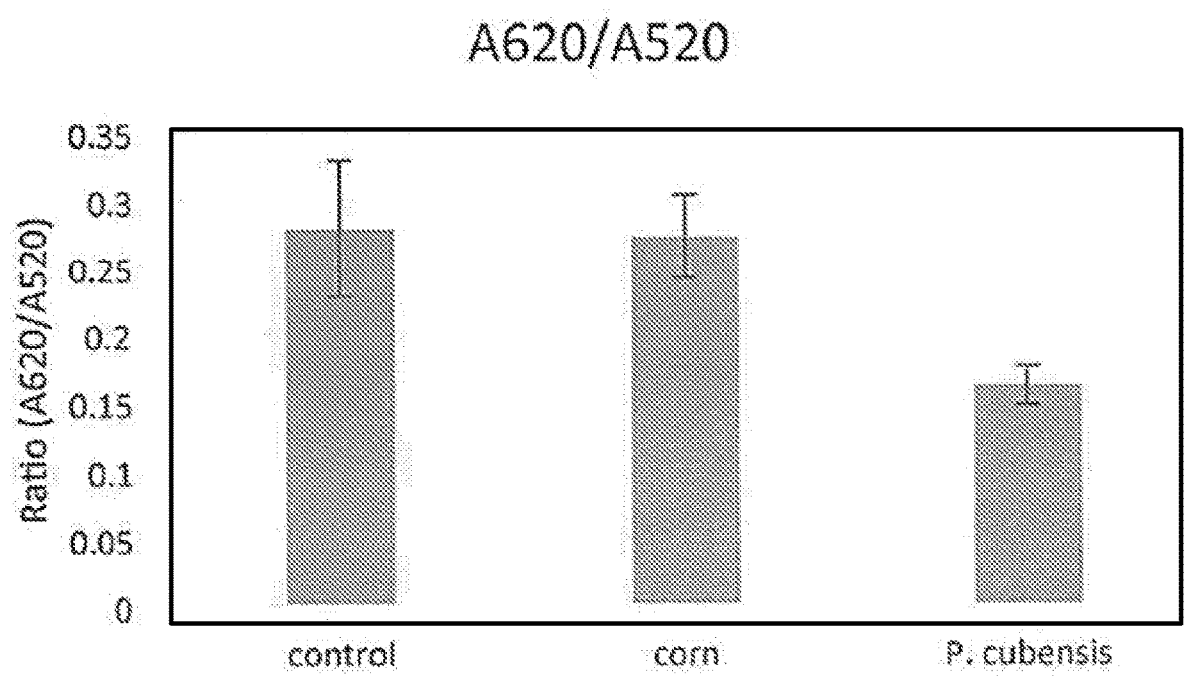
FIG. 7 is a graph illustrating the absorbance ratio of blue (A620/620 nm) to red (A520/520 nm) absorbance of water control, non-target corn DNA, and target *P. cubensis* DNA samples. A lower A620 nm/A520 nm ratio indicates target presence.

Sensitivity—Extracted Genomic DNA: The ability to detect low levels of pathogens, including under asymptomatic conditions, requires the development of diagnostic assays that offer both specificity and sensitivity. The results above demonstrate the specificity of this assay through the detection of plant-extracted DNA. The sensitivity of the assay was then evaluated using gDNA from the cucurbit downy mildew pathogen *Pseudoperonospora cubensis*. Cucurbit downy mildew is currently the primary threat in the U.S. limiting cucumber production, and the early detection of this pathogen, including the ability to detect the presence of the pathogen in fields before symptom development would enhance management and production. As shown in FIG. 5 (panel A), using a serial dilution of gDNA, ranging from 29 fM to 0.29 fM, a discernible, visual reduction in d-AuNP aggregation was observed to 2.9 fM, as compared to control reactions (i.e., no DNA). This decrease in d-AuNP aggregation relative to an increase in target DNA supports the hypothesis that the d-AuNP-DNA interaction is suitable not only for the quantitative detection of DNA, but also represents an advance in current limiting approaches (FIG. 5, panel B). Indeed, most detection methods employed at present require amplification of the target DNA (e.g., LAMP-based assays).

Sensitivity—Crude DNA from pathogen matrix: Next, to determine the sensitivity of this assay in the detection of crude DNA (i.e., non-extracted) samples, the sensitivity of the reaction was investigated using serially-diluted sporangia—the wind-dispersed spores—of *P. cubensis*. As shown in FIG. 5 (panel A), sporangia were serially diluted from 185 to 1.8 spores/µL, and the ground, crude lysates were incubated in the presence of AuNPs and the ssDNA probe to reveal optically distinct target detection of approximately 18.5 sporangia/µL when compared to no DNA control reactions. The linear relationship ($R^2=0.999$) between AuNP stabilization in the presence of DNA from pathogen spores demonstrates the quantitative abilities of this assay to detect pathogen DNA within crude matrices (FIG. 5, panel B). While the overall sensitivity of this assay with extracted gDNA is not especially low when compared to real-time PCR-based assays for *P. cubensis*, the disclosed method permits crude DNA detection of this pathogen under field settings with minimal instrumentation. Moreover, given the obligate nature of *P. cubensis*, the DNA samples analyzed herein may also contain contaminating non-target cucumber DNA, thus skewing the true detection limits of the disclosed method. Nonetheless, the assay described herein represents a marked improvement over currently available diagnostic methods.

Summary: The example illustrates a rapid and highly specific method for the detection of DNA, one that exploits colorimetric DNA sequence-specific detection using unmodified dextrin-capped AuNPs. This illustrated example utilizes the unique properties of gold nanoparticles coated with dextrin. The use of unmodified d-AuNPs to directly detect specific DNA sequences in reaction solution containing genomic DNA illustrated several advantages, including that 1) d-AuNPs have a wider range of stability to salt than c-AuNPs, 2) d-AuNPs adsorbed ssDNA enabling a DNA sequence-specific detection assay, and 3) the elevated ionic assay concentration alters DNA-DNA and d-AuNPs-DNA interactions allowing target stabilization of d-AuNPs and DNA detection within crude matrices. In total, the disclosed DNA-based nanoparticle assay permits the detection of DNA at limits several magnitudes lower than existing point of care approaches, including with the added advantage of not requiring expensive temperature-sensitive reagents. It is thought that DNA detection by d-AuNPs overcomes many challenges currently limiting nanotechnology adoption for field-deployable-based detection of pathogens affecting human health and food security through the cost of this assay (i.e., <$0.01 per reaction), as well as the increased synthesis sustainability over c-AuNPs, and the ability to specifically detect a plant pathogen's gDNA from a crude environmental matrix.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the apparatus, compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS LIST

10 sample or assay vessel
20 sample containing or suspected of containing a target DNA analyte
30 buffer solution
40 sample mixture
42 incubated solution
50 ionic species solution
60 solution-nanoparticle mixture
62 solution-nanoparticle mixture including stabilized metal nanoparticles
64 solution-nanoparticle mixture including destabilized metal nanoparticles
100 target DNA analyte (or double-stranded DNA (dsDNA))
102 first strand of dsDNA target analyte
104 second strand of dsDNA target analyte
104' unbound portion of second strand of dsDNA target analyte
150 non-target DNA
200 probe DNA (or single-stranded probe DNA (ssDNAp))
202 bound/hybridized probe DNA
204 free or unbound/non-hybridized probe DNA
300 probe DNA-target DNA complex
310 first region of probe DNA-target DNA complex
320 second region of probe DNA-target DNA complex 400 non-functionalized, carbohydrate-capped (stabilized) metal nanoparticles
410 stabilized metal nanoparticles
420 destabilized metal nanoparticles
500 probe DNA-target DNA-metal nanoparticle complex
510 first region of probe DNA-target DNA-metal nanoparticle complex
520 second region of probe DNA-target DNA-metal nanoparticle complex

What is claimed is:

1. A method for detection of a target analyte, the method comprising:
   combining (i) a sample containing or suspected of containing a target DNA analyte with (ii) a probe DNA that is complementary to the target DNA analyte, thereby forming a sample mixture;
   incubating the sample mixture under conditions sufficient to bind the probe DNA with any target DNA analyte present in the sample mixture, thereby forming an incubated solution comprising (i) a probe DNA-target DNA complex when the target DNA analyte is present in the sample, and (ii) free probe DNA when the target DNA analyte is not present in the sample;
   combining the incubated solution with a non-functionalized, carbohydrate-capped metal nanoparticle free from negatively charged polymer capping agents and an ionic species, thereby forming a solution-nanoparticle mixture; and
   incubating the solution-nanoparticle mixture under conditions sufficient to (i) at least partially stabilize the metal nanoparticle when the probe DNA-target DNA complex is present in the solution-nanoparticle mixture, and (ii) at least partially destabilize the metal nanoparticle when the target DNA analyte is not present in the sample.

2. The method of claim 1, further comprising:
   detecting a relative degree of metal nanoparticle stabilization after incubating the solution-nanoparticle mixture.

3. The method of claim 2, wherein detecting a relative degree of metal nanoparticle stabilization comprises detecting a color state of the solution-nanoparticle mixture after incubation.

4. The method of claim 1, wherein the target DNA analyte comprises double-stranded genomic DNA (dsDNAg) characteristic of a target analyte organism.

5. The method of claim 4, wherein the target analyte organism is selected from the group consisting of a virus, a bacterium, a mould, a fungus, and a plant.

6. The method of claim 4, wherein the target analyte organism is a plant pathogen.

7. The method of claim 1, wherein the sample comprises a plant extract and the target DNA analyte comprises a plant pathogen DNA.

8. The method of claim 7, wherein the sample comprises a crude plant extract.

9. The method of claim 1, wherein the probe DNA comprises a single-stranded probe DNA (ssDNAp).

10. The method of claim 1, wherein the single-stranded probe DNA has a length of 5 to 100 nucleotide bases.

11. The method of claim 1, wherein the sample mixture further comprises a buffer.

12. The method of claim 11, wherein the buffer comprises a phosphate-buffered saline (PBS) buffer.

13. The method of claim 1, wherein the sample mixture has a salt concentration of at least 40 mM.

14. The method of claim 1, wherein incubating the sample mixture to form the incubated solution comprises:
   denaturing the sample mixture under conditions sufficient to denature any target DNA analyte present in the sample mixture; and then
   annealing the sample mixture under conditions sufficient to hybridize any denatured target DNA analyte present in the sample mixture with the probe DNA, thereby forming the probe DNA-target DNA complex when the target DNA analyte is present in the sample.

15. The method of claim 1, wherein the probe DNA-target DNA complex comprises:
   a first region comprising a single-stranded probe DNA (ssDNAp) hybridized to a first strand of a double-stranded target DNA analyte (dsDNA); and
   a second region comprising a second strand of the double-stranded target DNA analyte (dsDNA) that is not bound to the first strand of the double-stranded target DNA analyte (dsDNA).

16. The method of 15, wherein, after incubation of the solution-nanoparticle mixture, a corresponding probe DNA-target DNA-metal nanoparticle complex comprises:
- a first region comprising a single-stranded probe DNA (ssDNAp) hybridized to a first strand of a double-stranded target DNA analyte (dsDNA);
- a second region comprising a second strand of the double-stranded target DNA analyte (dsDNA) that is not bound to the first strand of the double-stranded target DNA analyte (dsDNA); and
- the metal nanoparticle bound to the second strand of the double-stranded target DNA analyte in the second region.

17. The method of claim 1, wherein the non-functionalized, carbohydrate-capped metal nanoparticle comprises a gold nanoparticle and a dextrin capping agent on an outer surface of the gold nanoparticle.

18. The method of claim 1, wherein the non-functionalized, carbohydrate-capped metal nanoparticle is in the form of a non-functionalized, stabilized metal nanoparticle suspension composition comprising:
- water in sufficient amount to provide an aqueous medium; and
- a plurality of stabilized metal nanoparticles stably suspended in the aqueous medium, each stabilized metal nanoparticle comprising: (i) a metal nanoparticle core and (ii) a carbohydrate capping agent present as a layer on an outer surface of the metal nanoparticle core in an amount sufficient to stabilize the metal nanoparticle suspension.

19. The method of claim 1, wherein the non-functionalized, carbohydrate-capped metal nanoparticle is free from biomolecules and specific binding pair members which specifically bind to the target DNA analyte.

20. The method of claim 1, wherein the ionic species combined with the incubated solution and the non-functionalized, carbohydrate-capped metal nanoparticle comprises sodium chloride.

21. The method of claim 1, wherein the carbohydrate-capped metal nanoparticle is free from negatively charged capping agents.

22. The method of claim 1, wherein the carbohydrate-capped metal nanoparticle is free from capping agents other than carbohydrates.

23. The method of claim 1, wherein:
- (i) a maintained color state between initial and final solutions corresponds to the presence of the target DNA, and
- (ii) a changed color state between initial and final solutions corresponds to the absence of the target DNA.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
taattgtagt tacagtattc gtttg                                              25

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 2
aatcacagct tctatgtttt acat                                               24
```